US012607613B2

(12) United States Patent
Kevadiya et al.

(10) Patent No.: US 12,607,613 B2
(45) Date of Patent: Apr. 21, 2026

(54) GAS CHROMATOGRAPHY CALIBRATION TECHNIQUE USING LINEAR RATIOS

(71) Applicant: Halliburton Energy Services, Inc., Houston, TX (US)

(72) Inventors: Jhanvi Manishkumar Kevadiya, Houston, TX (US); Mathew Dennis Rowe, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 366 days.

(21) Appl. No.: 18/373,770

(22) Filed: Sep. 27, 2023

(65) Prior Publication Data

US 2025/0102481 A1     Mar. 27, 2025

(51) Int. Cl.
*G01N 30/86* (2006.01)
*B01D 53/02* (2006.01)
*G01N 30/32* (2006.01)
*G01N 33/28* (2006.01)
*G01N 30/02* (2006.01)

(52) U.S. Cl.
CPC ....... *G01N 30/8665* (2013.01); *B01D 53/025* (2013.01); *G01N 30/32* (2013.01); *G01N 33/2823* (2013.01); *G01N 2030/025* (2013.01); *G01N 2030/326* (2013.01)

(58) Field of Classification Search
CPC .................................................. G01N 30/8665
See application file for complete search history.

(56) References Cited

U.S. PATENT DOCUMENTS

| | | | | |
|---|---|---|---|---|
| 4,055,399 | A | * | 10/1977 | Parrish .................... E21B 47/11 436/27 |
| 9,140,674 | B2 | * | 9/2015 | DiSanzo ............ G01N 33/2823 |

(Continued)

FOREIGN PATENT DOCUMENTS

| | | | | |
|---|---|---|---|---|
| CN | 105675803 | A | | 6/2016 |
| EP | 0370870 | A1 | * | 5/1990 ......... G01N 33/0018 |

(Continued)

OTHER PUBLICATIONS

U.S. Appl. No. 17/587,978, filed Jan. 28, 2022.

(Continued)

*Primary Examiner* — John E Breene
*Assistant Examiner* — Alex T Devito
(74) *Attorney, Agent, or Firm* — Benjamin Ford; C. Tumey Law Group PLLC

(57) ABSTRACT

In general, in one aspect, embodiments relate to a method that includes varying at least a concentration of one or more components of a multi-component sample gas across at least a concentration range while introducing the multi-component sample gas into a gas chromatograph that includes one or more chromatographic columns, measuring concentrations of the one or more components with the gas chromatograph at a first calibration setting, determining one or more non-linearities of the measured concentrations at the first calibration setting, forming a second calibration setting based at least in part on the one or more non-linearities, and measuring concentrations of one or more components of another sample gas with the gas chromatograph at the second calibration setting.

20 Claims, 14 Drawing Sheets

(56) References Cited

U.S. PATENT DOCUMENTS

| | | | |
|---|---|---|---|
| 9,765,617 B2 | 9/2017 | Gosney et al. | |
| 10,001,465 B2 | 6/2018 | Mitchell | |
| 10,060,258 B2 | 8/2018 | Rowe | |
| 10,087,753 B2 | 10/2018 | Mitchell et al. | |
| 10,641,757 B2 | 5/2020 | Rowe | |
| 2013/0085674 A1 | 4/2013 | Zhdaneev et al. | |
| 2015/0226063 A1 | 8/2015 | Zuo et al. | |
| 2016/0123141 A1 | 5/2016 | Rowe et al. | |
| 2016/0178599 A1* | 6/2016 | Gisolf | G01N 33/28 |
| | | | 73/23.35 |
| 2016/0273353 A1 | 9/2016 | Rowe et al. | |
| 2017/0096893 A1 | 4/2017 | Graves et al. | |
| 2018/0156034 A1* | 6/2018 | Mitchell | E21B 49/08 |
| 2018/0156035 A1 | 6/2018 | DiFoggio et al. | |
| 2018/0245466 A1 | 8/2018 | Gosney et al. | |
| 2019/0368345 A1 | 12/2019 | Rowe et al. | |
| 2020/0256188 A1 | 8/2020 | Rowe | |
| 2021/0389239 A1 | 12/2021 | Rowe | |
| 2021/0404273 A1 | 12/2021 | Rowe | |
| 2022/0065105 A1 | 3/2022 | Rowe | |

FOREIGN PATENT DOCUMENTS

| | | | | |
|---|---|---|---|---|
| WO | WO-9410901 A1 * | 5/1994 | | A61B 5/6833 |
| WO | 2015076839 | 5/2015 | | |
| WO | 2023277913 | 1/2023 | | |

OTHER PUBLICATIONS

International Search Report and Written Opinion for International Patent Application No. PCT/US2023/077282 dated Jun. 21, 2024. PDF file. 8 pages.

\* cited by examiner

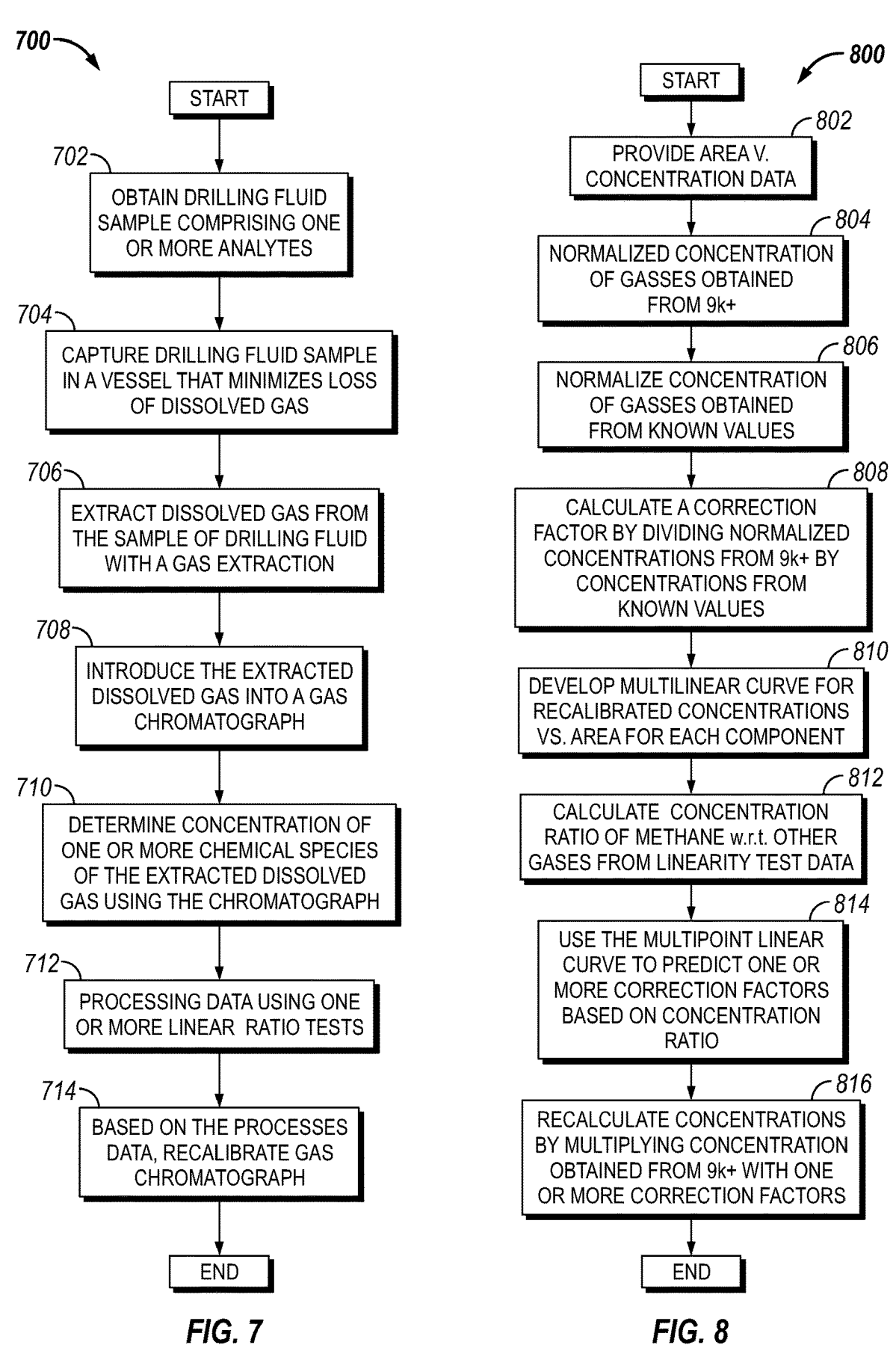
*FIG. 7*                    *FIG. 8*

GAS CHROMATOGRAPHY CALIBRATION TECHNIQUE USING LINEAR RATIOS

BACKGROUND

During wellbore operations, such as when drilling through a subterranean formation, formation fluids and gases may become entrapped in drilling fluid. These gases are extracted at the surface and analyzed using gas chromatography, mass spectrometry, or other analytical techniques, and equation of state calculations using this analysis data is then used to estimate the composition of the formation fluids. This information is often used to characterize the depositional environment and optimize drilling. For example, fluid analysis may allow an operator to identify and quantify fluids such as oil, gas, water, and/or other formation fluids at various depths within the subterranean formation.

In the context of gas chromatography, response curves are graphical representations showing the relationship between concentration of an analyte in a sample and a corresponding response signal generated by a detector of a gas chromatograph. As a general rule, the x-axis of a response curve is the known concentration of the analyte, and the y-axis is the response signal. Response curves are useful in that, since they establish relationships between concentration and response signal, they are used as a reference to estimate the concentrations of the analyte in unknown samples.

Multi-linear gas chromatography is a method of determining the concentration of multiple species in a sample using a single analysis. In traditional gas chromatography, a separate response curve is constructed for each individual component using standard solutions with known concentrations. However, multi-linear gas chromatography allows multiple components to be simultaneously determined in a single analysis without the need for separate response curves.

Response curves rendered using these multi-linear methods may be inaccurate, especially when they rely on small sample sizes. Specifically, these response curves may poorly fit data, may not adequately capture relationship between variables, may not fully account for the curvature of a response curve, or may otherwise introduce error.

BRIEF DESCRIPTION OF THE DRAWINGS

These drawings illustrate certain aspects of some of the examples of the present invention and should not be used to limit or define the invention.

FIG. 7 illustrates a workflow for performing calibration of a gas chromatograph according to one or more examples of the present disclosure.

FIG. 8 illustrates a workflow for performing data processing during calibration of a gas chromatograph according to one or more examples of the present disclosure.

DETAILED DESCRIPTION

Figure 1:
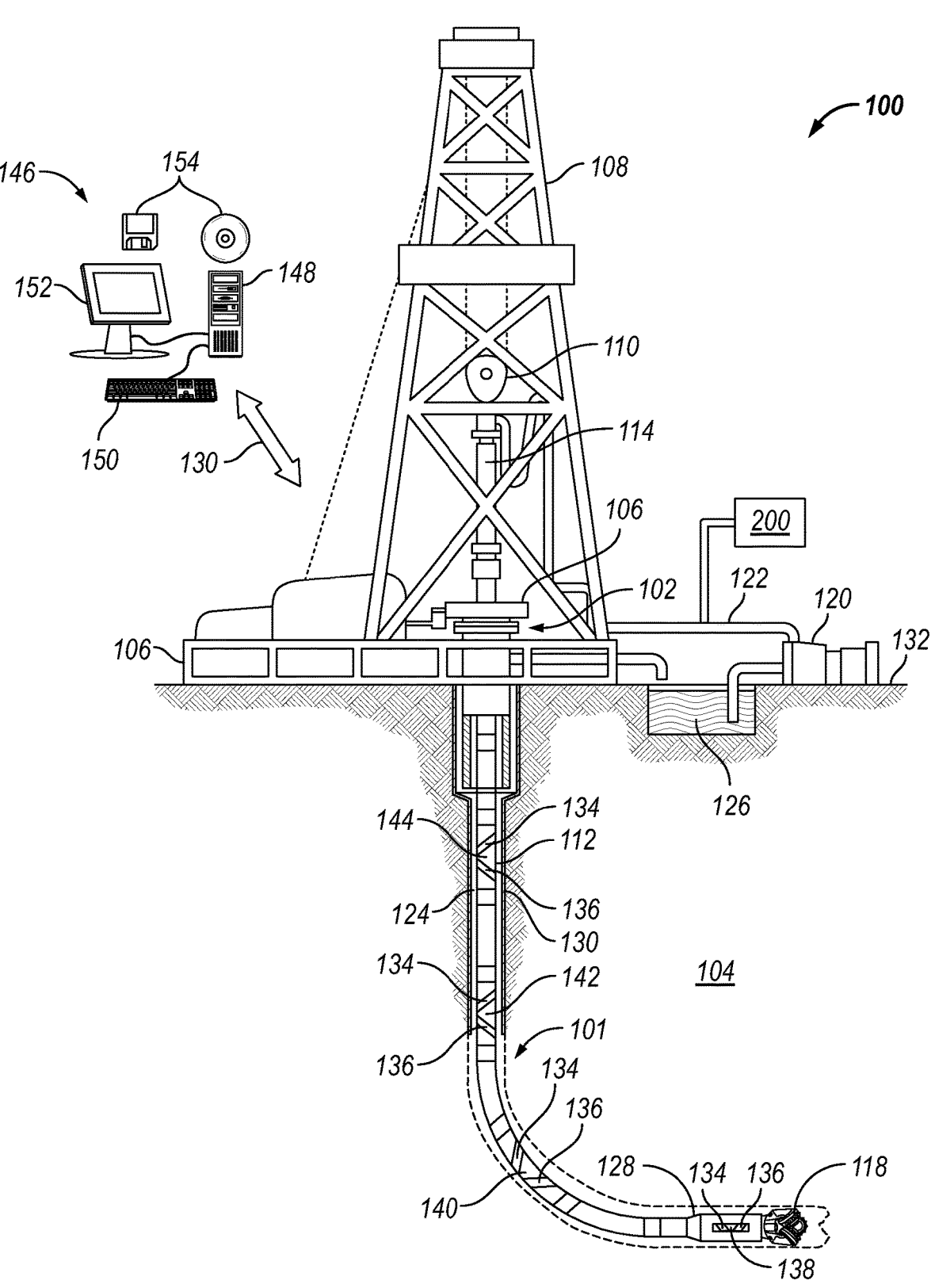
FIG. 1 illustrates a drilling system according to one or more examples of the present disclosure.

Disclosed herein are methods and systems for performing gas chromatography and, more particularly, disclosed are methods and systems that include performing analysis and calibration of a gas chromatograph using a linear ratio test. Also disclosed herein are methods and systems for using one or more calibrated gas chromatographs during a drilling operation.

The methods and systems described herein may be performed in conjunction with equipment at a rig site. Equipment used at a rig site may include, to use non-limiting examples, any equipment which would commonly be used during drilling, well stimulation, and/or production of a hydrocarbon-bearing reservoir. The methods and systems disclosed herein may address, without limitation, the problems previously stated by this disclosure. Specifically, the present disclosure may provide methods and systems for implementing linear ratio tests for filling in missing calibration data from a basic calibration.

As alluded to, basic calibration a gas chromatograph, i.e., without the linear ratio test(s) of the present disclosure, may not reliably measure the concentrations of various species present within a sample being tested by the gas chromatograph. Especially in situations where there are a large number of (e.g., greater than 5) components within a sample, and where only sparse amounts of data is available, results rendered by the gas chromatograph may poorly fit data, may not adequately capture relationships between variables, may not fully account for curvature of a response curve, or may otherwise introduce error. This lack of reliability is compounded when, for example, there are plural, complex interactions between the individual species of the sample being measured by the gas chromatograph, which further throws into question the accuracy of the response. In practice, large amounts of testing in a laboratory using an inordinate number of tests and samples are required to address these issues, or the issues are not addressed, and suboptimal data is used to inform important decisions regarding reservoir operations. It may be impractical in some situations to perform the large amount of testing required to render data that is reliable and accurate, and adverse consequences may result from poor understanding of the composition of the formation fluids.

The linear ratio test is a specific type of procedure used to assess deviation of linear ratios to determine linearity or non-linearity of a gas chromatograph. In examples, the linear ratio test involves determining linear ratios between components and assessing the linearity or non-linearity of the gas chromatograph based on deviation or lack of deviation of the linear ratios. Results of the linear ratio test(s) may be used to determine correction factors, whereby curve-fitting or an equivalent method is used to predict additional correction factors. A second calibration setting, with the second calibration setting relying on the predicted correction factors may then be used to render more accurate response curves, for example, multi-linear curves that more accurately represent the actual concentrations of the components within the sample being tested.

As used herein, "8900" refers to an isothermal, isobaric gas chromatography system having a single chromatographic column and FID, along with its associated software package.

As used herein, "9250" or "9K+" refers to a gas chromatography system having two flame ionization detectors ("FIDs") and two chromatographic columns, along with its associated software package. Unlike 8900, column temperatures and pressures of 9250 are dynamic as opposed to fixed.

As used herein, "C1" is methane, "C2" is ethane, "C3" is propane, "nC4" or "C4" is butane, "iC4" is isobutane, "nC5" or "C5" is pentane, and "iC5" is isopentane.

As used herein, "linear ratios" refer to concentration ratios. Linear ratios may include, for example, C1/C2, C1/C3, C1/C4, C2/C3, iC4/nC4, iC5/nC5, etc.

While some of the figures specifically refer to drilling systems, it should be understood that the principles herein taught with respect to gas calibration using linear ratios are not limited only to drilling systems. For example, the principles and teachings taught herein may be applied during production operations, wellbore intervention operations, hydraulic fracturing, enhanced oil recovery operations, combinations thereof, or the like.

FIG. 1 illustrates a drilling system 100. As illustrated, drilling system 100 may include a drilling platform 106 may support a derrick 108 having a traveling block 110 for raising and lowering drill string 112. Drill string 112 may include, but is not limited to, drill pipe and coiled tubing, as generally known to those skilled in the art. A kelly 114 may support drill string 112 as it may be lowered through a rotary table 116. A drill bit 1218 may be attached to the distal end of drill string 112 and may be driven either by a downhole motor and/or via rotation of drill string 112 from surface 132. Without limitation, drill bit 118 may include roller cone bits, PDC bits, natural diamond bits, any hole openers, reamers, coring bits, and the like. As drill bit 118 rotates, it may create and extend wellbore 101 that penetrates various subterranean formations 104.

Generally, wellbore 101 may include horizontal, vertical, slanted, curved, and other types of wellbore geometries and orientations. Wellbore 101 may be cased or uncased. In examples, wellbore 101 may include a metallic material. By way of example, the metallic member may be a casing, liner, tubing, or other elongated steel tubular disposed in wellbore 101.

As illustrated, wellbore 101 may extend through subterranean formation 104. As illustrated in FIG. 1, wellbore 101 may extend generally vertically into the subterranean formation 104, however wellbore 101 may extend at an angle through subterranean formation 104, such as for horizontal and slanted wellbores. For example, although FIG. 1 illustrates a vertical or low inclination angle well, high inclination angle or horizontal placement of the well and equipment may be possible. It should further be noted that while FIG. 1 generally depicts a land-based operation, those skilled in the art may recognize that the principles described herein are equally applicable to subsea operations that employ floating or sea-based platforms and rigs, without departing from the scope of the disclosure.

With continued reference to FIG. 1, a pump 120 may circulate drilling fluid through a feed pipe 122 to kelly 114, downhole through interior of drill string 112, through orifices in drill bit 118, back to surface 132 via annulus 124 surrounding drill string 112, and into a retention pit 126. Drill string 112 may begin at wellhead 102 and may traverse wellbore 101. Drill bit 118 may be attached to a distal end of drill string 112 and may be driven, for example, either by a downhole motor and/or via rotation of drill string 112 from surface 132. Drill bit 118 may be a part of bottom hole assembly 128 at distal end of drill string 112.

As illustrated, drilling system 100 may include gas extraction system 200. Gas extraction system 200 may include a gas extractor, to be discussed later in detail. As illustrated, gas extraction system 200 may be configured to receive sampled drilling fluid from feed pipe 122, however, it should be understood that gas extraction system 200 may be alternatively configured to extract dissolved gas of any of the fluids passing through any part of drilling system 100. At the surface 132, circulated fluid exits annulus 124 and may be conveyed, continuously or periodically, to gas extraction system 200. As will be also discussed later in detail, one or more gas chromatograph(s) are coupled to gas extraction system 200 for performing gas chromatography on the sample gas extracted by gas extraction system 200.

Systems and methods of the present disclosure may be implemented, at least in part, with information handling system 146. Information handling system 146 may include any instrumentality or aggregate of instrumentalities operable to compute, estimate, classify, process, transmit, receive, retrieve, originate, switch, store, display, manifest, detect, record, reproduce, handle, or utilize any form of information, intelligence, or data for business, scientific, control, or other purposes. For example, an information handling system 146 may be a personal computer, two or more computers working in a network, a network storage device, or any other suitable device and may vary in size, shape, performance, functionality, and price. Information handling system 146 may include random access memory (RAM), one or more processing resources such as a central processing unit (CPU) 148 or hardware or software control logic, ROM, and/or other types of nonvolatile memory. Additional components of the information handling system 146 may include one or more disk drives, one or more network ports for communication with external devices as well as an input device 150 (e.g., keyboard, mouse, etc.) and output devices, such as a video display 152. Information handling system 146 may also include one or more buses operable to transmit communications between the various hardware components.

Alternatively, or additionally, systems and methods of the present disclosure may be implemented, at least in part, with non-transitory computer-readable media 154. Non-transitory computer-readable media 154 may include any instrumentality or aggregation of instrumentalities that may retain data and/or instructions for a period of time. Non-transitory computer-readable media 154 may include, for example, storage media such as a direct access storage device (e.g., a hard disk drive or floppy disk drive), a sequential access storage device (e.g., a tape disk drive), compact disk, CD-ROM, DVD, RAM, ROM, and electrically erasable programmable read-only memory (EEPROM), and/or flash memory. In examples, communications media may be used to move information from one non-transitory computer-readable media 154 to another. Communications media may comprise wires, optical fibers, microwaves, radio waves, and other electromagnetic and/or optical carriers; and/or any combination of the foregoing.

As illustrated, communication link 130 (which may be wired or wireless, for example) may be provided that may transmit data from downhole tool 138, gas extraction module 200, and one or more gas chromatographs operationally coupled to gas extraction module 200 to an information handling system 146 at surface 132. Information handling system 146 may include a central processing unit 148, a video display 152, an input device 150 (e.g., keyboard, mouse, etc.), and/or non-transitory computer-readable media 154 (e.g., optical disks, magnetic disks) that may store code representative of the methods described herein. In addition to, or in place of processing at surface 132, processing may occur downhole.

Figure 2:
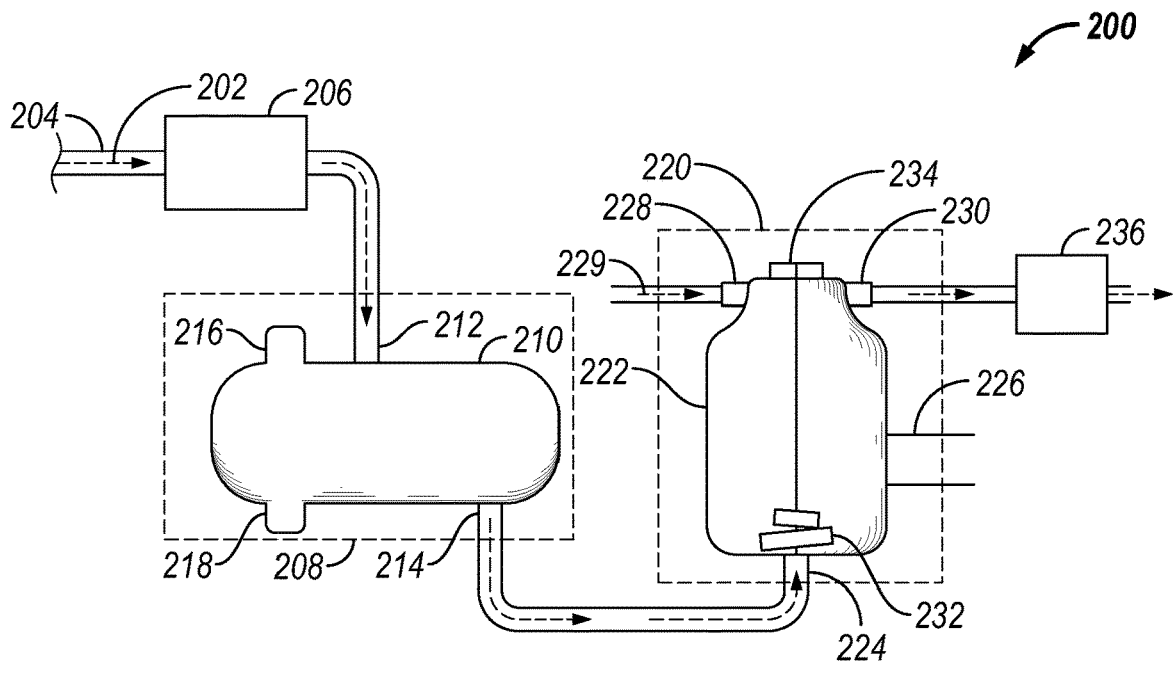
FIG. 2 illustrates a system for performing gas extraction and gas analysis according to one or more examples of the present disclosure.

FIG. 2 is a diagram of an example gas extraction system 200 that extracts gases from a drilling fluid sample, according to some examples. The gas extraction system 200 may be included with a drilling system such as the drilling system 100 and may be in selective fluid communication with a flow of drilling fluid through the drilling system, such as at access points similar to those shown with reference to FIG. 1, or alternatively, at any suitable access point of drilling system 100 such that gas extraction system 200 is in fluidic communication with a flow path of drilling system 100. With continued reference to FIG. 2, the gas extraction system 200 may receive a drilling fluid sample 202 through a fluid conduit or pipe 204 that is in selective fluid communication with the flow of drilling fluid. As described above, drilling fluid samples may be taken periodically or continuously from the flow of drilling fluid through a fluid circulation system during drilling operation, and drilling fluid sample 202 may comprise one of those continuous or periodic samples. The gas extraction system 200 may comprise one or more pumps 206 that push the drilling fluid sample toward a sample-temperature controller 208 of the gas extraction system 200. Sample-temperature controller 208 may be configured to alter or maintain the temperature of drilling fluid sample 202 at a set temperature, which may be hotter, cooler, or the same as the temperature of sample 202 as it enters the gas extraction system 200. In the example shown, sample-temperature controller 208 comprises a shell and tube heat exchanger with two sets of fluid inlets and outlets: a first inlet 212 and first outlet 214, and a second inlet 216 and second outlet 218. One or more sets of fluid inlets and outlets may correspond to a different, segregated fluid pathway through shell 210. For example, the second inlet 216 and second outlet 218 may correspond to a fluid pathway comprising a system of sealed tubes (not shown) located within shell 210, and the first inlet 212 and first outlet 214 may correspond to a fluid pathway in which fluid flows around the system of sealed tubes. The system of sealed tubes may comprise u-tubes, single-pass straight tubes, double-pass straight tubes, or other configurations.

In certain examples, sample 202 may enter shell 210 through first inlet 212 and exit through first outlet 214. A second fluid or gas may enter shell 210 through second inlet 216 and exit through second outlet 218. Either the second fluid or drilling fluid sample 202 may flow through the system of sealed tubes. The second fluid may be at or near a desired set temperature for drilling fluid sample 202, and energy transfer may occur between sample 202 and the second fluid through the tubes, which may conduct thermal energy, until sample 202 has reached the desired set temperature. Notably, although a shell and tube heat exchanger are described herein, sample-temperature controller 208 may comprise other types of heat exchangers, including, but not limited to, thermoelectric, electric, and finned tube heat exchanger that are driven by electricity, gas, or liquid; u-tube heat exchangers; etc.

Once at or near the set temperature, drilling fluid sample 202 may be received at a gas extractor 220 of the gas extraction system 200, the gas extractor 220 being in fluid communication with sample-temperature controller 208. Example gas extractors include, but are not limited to, continuously stirred vessels, distillation columns, flash columns, separator columns, or any other vessel that allows for the separation and expansion of gas from liquids and solids. In the example shown, the gas extractor 220 comprises a vessel 222 that receives sample 202 through a fluid inlet 224 and further comprises a fluid outlet 226 through which a portion of sample 202 will flow after a gas extraction process. The gas extractor 220 may further comprise impeller 232 within vessel 222 to agitate sample 202 as it enters vessel 222. The impeller 232 may be driven by a motor 234 that rotates the impeller to create a turbulent flow of sample 202 within vessel, which causes gases trapped within the solids and liquids of sample 202 to be released into vessel 222. Although impeller 232 is shown it is possible to use other types of agitators.

Gases within vessel 222 that are released from sample 202 through the agitation process may be removed from vessel through a gas outlet 230. In certain examples, vessel 222 may comprise a gas inlet 228, and at least one carrier gas 229 may be introduced into vessel 222 through the gas inlet 228. Carrier gases 229 may comprise atmospheric or purified gases that are introduced into vessel 222 to aide in the movement of the extracted gases to a gas outlet 230. The carrier gases may have known chemical compositions such that their presence can be accounted for when the extracted gases from gas outlet 230 are analyzed. Suitable gases to be used as carrier gas include, without limitation, nitrogen (N$_2$), helium (He), hydrogen (H$_2$), noble gases, combinations thereof, and the like.

Although sample-temperature controller 208 and gas extractor 220 are shown as separate devices, it may be possible to combine the functionality into a single device. For example, heat exchange may be accomplished through vessel 222, bringing sample 202 to a set temperature while it is in vessel 222. In other examples, sample-temperature controller 208 may be optional, and sample 202 may be directed to the extractor 220 without flowing through sample-temperature controller 208. In certain examples, the gas outlet 230 of the extractor 220 may be coupled to a pump 236 which may deliver the extracted gas sample out from the extractor 220. One or more gas chromatographs may be operationally coupled to gas outlet 230. Gas chromatography may be performed on the extracted gas sample with one or more gas chromatographs.

Figure 3:
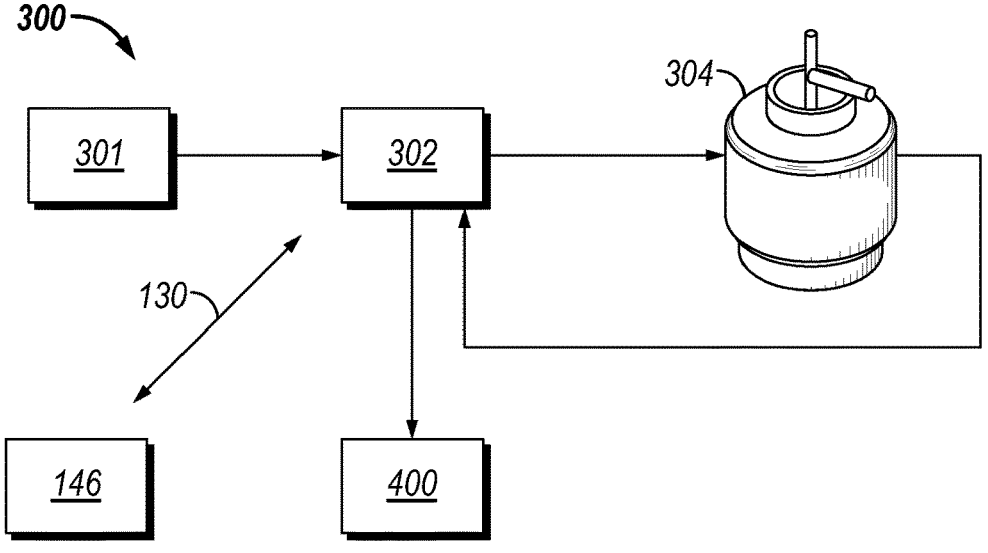
FIG. 3 illustrates a system for performing calibration of a gas chromatograph according to one or more examples of the present disclosure.

FIG. 3 illustrates gas extraction and chromatography system 300 for performing gas extraction and chromatographic analysis on a fluid sample 301, according to one or more examples of the present disclosure. As previously alluded to, fluid sample 301 may be a drilling fluid sample or another fluid sample from various types of wellbore operations. Gas extraction and chromatography system 300 includes gas extraction system 302. An example of the gas extraction system 302 is the gas extraction system 200 illustrated in FIGS. 1 and 2. Alternative configurations may be possible, provided that the gas extraction system 200 extracts sample gas from the drilling fluid 301.

Gas extraction and chromatography system 300 also includes a gas chromatograph 400, information handling system 146, and optionally, vessel 304. Gas chromatograph 400 may include a single chromatographic column, or multiple (e.g., two). Separation of sample gas occurs within the chromatographic column(s) prior to detection by one or more detectors, to be discussed later in detail (e.g., referring to FIG. 5). The gas chromatograph 400 may be isobaric and/or isothermal.

The vessel 304 may be any suitable vessel configured to circulate extracted gases from gas extractor 302. In examples, the vessel 304 may be purged to preferentially remove one or more components of the sample gas entering gas chromatograph 400. This allows in some examples precise control over the composition of the sample gas being measured, such that a comparison between known and estimated values may be performed. Where used, purging may be performed by removing extracted gas at a controlled rate from the top or bottom of the vessel 304, and/or by adding a non-interfering gas to the vessel 34 at a controlled rate. In one or more examples, purging may be either a "continuous bottom purge," i.e., "bottom purge," or a "continuous top purge," i.e., "top purge." A continuous bottom purge preferentially removes the heavier components (e.g., pentane, isopentane) from sample gas during calibration of the gas chromatograph 400, whereas a continuous top purge preferentially removes the lighter components (e.g., ethane, propane, butane).

In operation, a fluid sample 301 is input into the gas extraction system 302. Once the measured concentration of at least one type of species reaches a threshold, the gas extraction system 302 inputs the fluid sample 301 into vessel 304. For example, once a measured concentration species reaches 100 parts per million (PPM) for the drilling fluid sample, the gas extraction system 302 can input the drilling fluid sample into vessel 304. Also, an output of the gas extraction system 302 is coupled to an input of gas chromatograph 400 that is configured to measure or otherwise determine concentrations of species based on the extracted gas received from gas extraction system 302. Storage of the sample in vessel 304 can minimize dissolved formational gas loss.

Additionally, an output of vessel 304 is coupled back to an input of the gas extraction system 302. The drilling fluid sample can then be recirculated through the gas extraction system 302 continuously to extract dissolved gas while flowing extracted gas extracted in a gas extractor within gas extraction system 302 (e.g., gas extractor 220) to gas chromatograph 400 for concentration measurement and other analysis. Gas chromatograph 400 may be configured to determine concentration of one or more species of the extracted gas over time.

In some examples, gas chromatograph 400 is configured to determine species of the drilling fluid sample that includes methane, ethane, propane, isobutane, butane, isopentane, and pentane. Information handling system 146 is communicatively coupled to any individual component and/or combination of components of gas extraction and chromatography system 300 including, without limitation, gas extraction system 302, gas chromatograph 400, and any combination thereof. For example, information handling system 146 is communicatively coupled to gas chromatograph 400 to receive values of the concentration of one or more species of the extracted gas over time. As further described below, information handling system 146 may be configured to fill in missing calibration data using linear ratios, plot concentrations of one or more species versus time, and the like. Information handling system 146 may also be configured to generate a response signal per analyte concentration curve for one or more components of sample gas based on, for example, periodic measurements of gas chromatograph 400. As used herein, "analyte" broadly refers to one or more species or components of a sample, and which may be either of interest or not, such as an inert species.

Gas extraction and chromatography system 300 may be equipped with a syringe, injection device, an automated injection system (e.g., autosampler), or the like, (i.e., "injector") for injection sample gas into a mobile phase (i.e., "carrier gas") of gas chromatograph 400. An effluent of gas extraction system 302 may thus comprise or be combined with carrier gas and may be injected into gas chromatograph 400.

Figure 4:
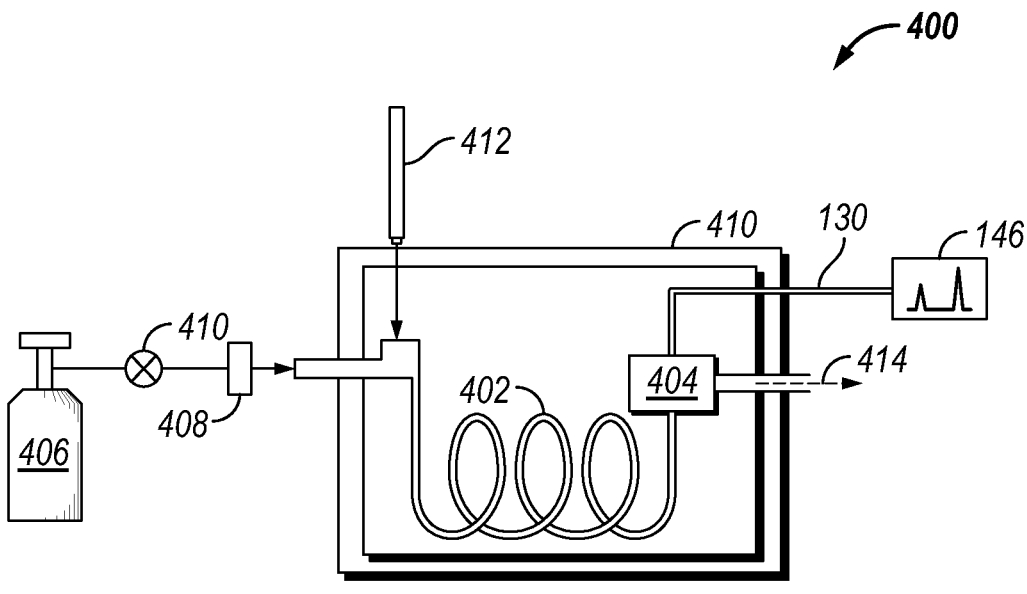
FIG. 4 illustrates a gas chromatograph according to one or more examples of the present disclosure.

FIG. 4 illustrates a gas chromatograph 400 in accordance with examples of the present disclosure. As illustrated, gas chromatograph 400 generally includes one or more chromatographic columns 402, one or more detectors 404, an information handling system 146, and a source 406 of carrier gas. One or more flow control devices 408 may be disposed between source 406 and chromatographic column 402, and a pressure regulator may also be disposed between source 406 and flow control device 408, as illustrated. Chromatographic column 402 may be disposed within a temperature-controlled oven 410, where temperature may be controlled or maintained by information handling system 146. An injection device 412 may be disposed at gas chromatograph 400 to inject, in batches or continuously, one or more gases into carrier gas flowing through chromatographic column 402. Injection device 412 may comprise, for example, an autosampler, syringe, diffuser, automated injection system, or other injector.

The gas being injected into carrier gas flowing through gas chromatograph 400 may comprise, originate from, or be in fluidic communication with an effluent of gas extractor 302 (e.g., referring to FIG. 3). As such, the injected gas may comprise extracted dissolved gas from a drilling fluid sample or other wellbore fluid, to use non-limiting examples.

Detector 404 comprises one or more detectors. The function of detector 404 is to measure the at least partially separated components of the gas flowing through chromatographic column 402. These measurements are transmitted in one form or another to information handling system 146, where data processing occurs. Measurements may include, for example, one or more response signals of detector 404. Exemplary and non-limiting detectors which may be used as detector 404 include: flame ionization detector (FID), thermal conductivity detector (TCD), alkali flame detector (AFD), alkali flame ionization detector (AFID), flame photometric detector (FPD), catalytic combustion detector (CCD), discharge ionization detector (DID), electron capture detector (ECD), nitrogen-phosphorus detector (NPD), dry electrolytic conductivity detector (DELCD), mass spectrometer (MS or GC-MS), vacuum ultraviolet (UVU), electrolytic conductivity detector (EICD), helium ionization detector (IRD), photo-ionization detector (PID), pulsed discharge ionization detector (PDD), thermionic ionization detector (TID), and any combinations thereof. Detector 404 may alternatively comprise any suitable device for detection of analytes after chromatographic column 406. Depending on the composition of a gas being measured, detection of analytes with detector 410 produces a corresponding response signal. After being analyzed by detector 404, gas passed through gas chromatograph 400 may be disposed of as waste effluent 414.

Flow control device 408 is a device that controls the flow of diluent to a gas entering gas chromatograph 400. In examples, flow control device 408 comprises a mass flow controller (MFC). Alternative, non-limiting examples of suitable controllers to be used as flow control device 408 include thermal mass flow controllers, Coriolis gas flow controllers, differential pressure mass flow controllers, volumetric mass flow controllers, pressure-based mass flow controllers, sonic nozzle mass flow controllers, MEMS-based (microelectromechanical systems-based) mass flow controllers, combinations thereof, and the like. In addition to controlling flow, flow control device 408 may also be equipped with sensors to monitor the flow. Such measurements with flow sensors may be transmitted or relayed to information handling system 146. Flow sensors may include, for example, differential pressure (DP) sensors, thermal sensors, Coriolis flow sensors, electromagnetic flow sensors, ultrasonic flow sensors, vortex shedding sensors, positive displacement sensors, turbine flow sensors, pressure sensors, combinations thereof, and the like.

In one or more examples, gas injected into gas chromatograph 400 by injection device 412 may be diluted with diluent. Diluent may be used during calibration to ensure an appropriate composition and/or concentration of analyte(s) in the gas. For example, it may be desired to measure a sample across a range of analyte concentrations. In this manner, the composition of the gas may be controlled to ensure that the concentration(s) of one or more of the analytes are varied over time. While not shown, it should be understood that in examples where diluent is used to dilute a gas entering gas chromatograph 400 over time, another flow control device 408 may be used to regulate a flow of diluent into a sample gas being injected into gas chromatograph 400. In this way, composition of a gas being measured by gas chromatograph 400 may be controlled over time as flow control device 408 varies the concentration of analyte(s). As discussed, a range of concentrations allows response curves to be rendered from the various response signals produced by gas chromatograph 400. Selection of one or more species for a diluent may be useful for generating the appropriate response curves for a particular sample gas, analyte, and/or combination of analytes in a gas. A diluent may comprise at least one inert species and at least one species of interest, for example, $N_2$ and pentane. Non-limiting examples of suitable diluents to be used in accordance with the present disclosure include one or more target and/or non-target analytes, methane, ethane, propane, butane, pentane, hexane, a $C_1$ to $C_{15}$ hydrocarbon, alkanes, alkenes, combinations thereof, and the like.

As illustrated in FIGS. 3 and 4, various system components of gas extraction and chromatography system 300 and/or gas chromatograph 400 may be communicatively coupled with information handling system 146 via communication link 402. In examples, measurements of gas chromatograph 400 are transmitted in real-time to information handling system 146. Communication between information handling system 146 and gas extraction and chromatography system 300 via communication link 130 may be performed in real-time. As used herein, "real-time" may be generally understood to relate to a system, apparatus, or method in which a set of input data is processed and available for use within 100 milliseconds ("ms"). In further examples, the input data may be processed and available for use within 90 ms, within 80 ms, within 70 ms, within 60 ms, within 50 ms, within 40 ms, within 30 ms, within 20 ms, or any ranges therebetween. In some examples, real-time may relate to a human's sense of time rather than a machine's sense of time. For example, processing which results in a virtually immediate output, as perceived by a human, may be considered real-time processing.

Figure 5:
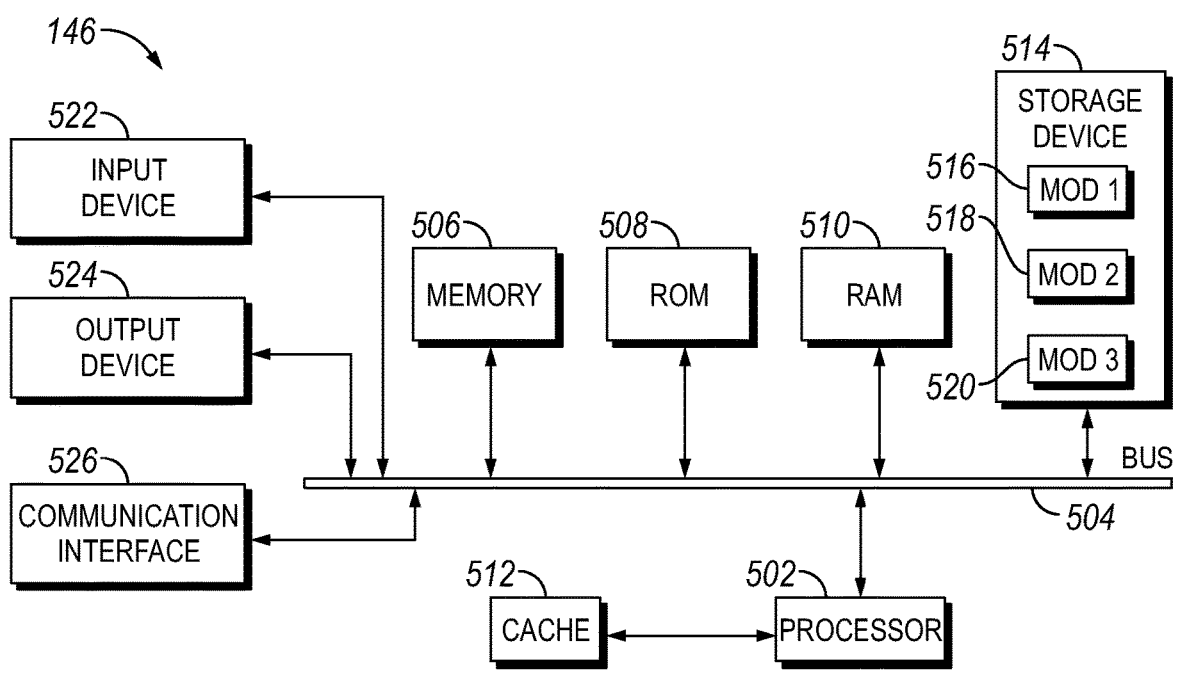
FIG. 5 illustrates a schematic of an information handling system according to one or more examples of the present disclosure.

FIG. 5 illustrates an example information handling system 146 which may be employed to perform various steps, methods, and techniques disclosed herein. Persons of ordinary skill in the art will readily appreciate that other system examples are possible. As illustrated, information handling system 146 comprises a processing unit (CPU or processor) 502 and a system bus 504 that couples various system components including system memory 506 such as read only memory (ROM) 508 and random-access memory (RAM) 510 to processor 502. Processors disclosed herein may all be forms of this processor 502. Information handling system 146 may comprise a cache 512 of high-speed memory connected directly with, in close proximity to, or integrated as part of processor 502. Information handling system 146 copies data from memory 506 and/or storage device 514 to cache 512 for quick access by processor 502. In this way, cache 512 provides a performance boost that avoids processor 502 delays while waiting for data. These and other modules may control or be configured to control processor 502 to perform various operations or actions. Other system memory 506 may be available for use as well. Memory 506 may comprise multiple different types of memory with different performance characteristics. It may be appreciated that the disclosure may operate on information handling system 146 with more than one processor 502 or on a group or cluster of computing devices networked together to provide greater processing capability. Processor 502 may comprise any general-purpose processor and a hardware module or software module, such as first module 516, second module 518, and third module 520 stored in storage device 514, configured to control processor 502 as well as a special-purpose processor where software instructions are incorporated into processor 502. Processor 502 may be a self-contained computing system, containing multiple cores or processors, a bus, memory controller, cache, etc. A multi-core processor may be symmetric or asymmetric. Processor 502 may comprise multiple processors, such as a system having multiple, physically separate processors in different sockets, or a system having multiple processor cores on a single physical chip. Similarly, processor 502 may comprise multiple distributed processors located in multiple separate computing devices but working together such as via a communications network. Multiple processors or processor cores may share resources such as memory 506 or cache 512 or may operate using independent resources. Processor 502 may comprise one or more state machines, an application specific integrated circuit (ASIC), or a programmable gate array (PGA) including a field PGA (FPGA).

One or more individual component discussed above may be coupled to system bus 504, which may connect one or more and every individual component to one or more other. System bus 504 may be any of several types of bus structures including a memory bus or memory controller, a peripheral bus, and a local bus using any of a variety of bus architectures. A basic input/output (BIOS) stored in ROM 508 or the like, may provide the basic routine that helps to transfer information between elements within information handling system 146, such as during start-up. Information handling system 146 further comprises storage devices 514 or computer-readable storage media such as a hard disk drive, a magnetic disk drive, an optical disk drive, tape drive, solid-state drive, RAM drive, removable storage devices, a redundant array of inexpensive disks (RAID), hybrid storage device, or the like. Storage device 514 may comprise software modules 516, 518, and 520 for controlling processor 502. Information handling system 146 may comprise other hardware or software modules. Storage device 514 is connected to the system bus 504 by a drive interface. The drives and the associated computer-readable storage devices provide nonvolatile storage of computer-readable instructions, data structures, program modules and other data for information handling system 146. In one aspect, a hardware module that performs a particular function comprises the software component stored in a tangible computer-readable storage device in connection with the necessary hardware components, such as processor 502, system bus 504, and so forth, to carry out a particular function. In another aspect, the system may use a processor and computer-readable storage device to store instructions which, when executed by the processor, cause the processor to perform operations, a method, or other specific actions. The basic components and appropriate variations may be modified depending on the type of device, such as whether information handling system 146 is a small, handheld computing device, a desktop computer, or a computer server. When processor 502 executes instructions to perform "operations", processor 502 may perform the operations directly and/or facilitate, direct, or cooperate with another device or component to perform the operations.

As illustrated, information handling system 146 employs storage device 514, which may be a hard disk or other types of computer-readable storage devices which may store data that are accessible by a computer, such as magnetic cassettes, flash memory cards, digital versatile disks (DVDs), cartridges, random access memories (RAMs) 510, read only memory (ROM) 508, a cable containing a bit stream and the like, may also be used in the exemplary operating environment. Tangible computer-readable storage media, computer-readable storage devices, or computer-readable memory devices, expressly exclude media such as transitory waves, energy, carrier signals, electromagnetic waves, and signals per se.

To enable user interaction with information handling system 146, an input device 522 represents any number of input mechanisms, such as a microphone for speech, a touch-sensitive screen for gesture or graphical input, keyboard, mouse, motion input, speech and so forth. An output device 524 may also be one or more of a number of output mechanisms known to those of skill in the art. In some instances, multimodal systems enable a user to provide multiple types of input to communicate with information handling system 146. Communications interface 526 generally governs and manages the user input and system output. There is no restriction on operating on any particular hardware arrangement and therefore the basic hardware depicted may easily be substituted for improved hardware or firmware arrangements as they are developed.

As illustrated, one or more individual components described above is depicted and disclosed as individual functional blocks. The functions these blocks represent may be provided through the use of either shared or dedicated hardware, including, but not limited to, hardware capable of executing software and hardware, such as a processor 502, that is purpose-built to operate as an equivalent to software executing on a general-purpose processor. For example, the functions of one or more processors presented in FIG. 5 may be provided by a single shared processor or multiple processors. (Use of the term "processor" should not be construed to refer exclusively to hardware capable of executing software.) Illustrative examples may comprise microprocessor and/or digital signal processor (DSP) hardware, read-only memory (ROM) 508 for storing software performing the operations described below, and random-access memory (RAM) 510 for storing results. Very large-scale integration (VLSI) hardware examples, as well as custom VLSI circuitry in combination with a general-purpose DSP circuit, may also be provided.

Figure 6:
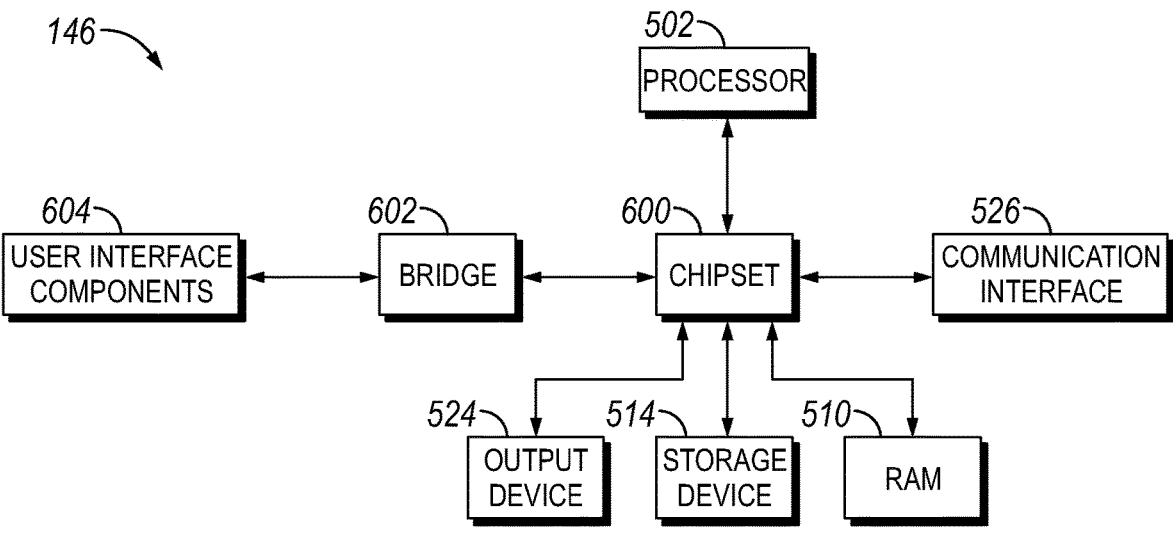
FIG. 6 illustrates a schematic of a chip set for an information handling system according to one or more examples of the present disclosure.

FIG. 6 illustrates an example information handling system 146 having a chipset architecture that may be used in executing the described method and generating and displaying a graphical user interface (GUI). Information handling system 146 is an example of computer hardware, software, and firmware that may be used to implement the disclosed technology. Information handling system 146 may comprise a processor 502, representative of any number of physically and/or logically distinct resources capable of executing software, firmware, and hardware configured to perform identified computations. Processor 502 may communicate with a chipset 600 that may control input to and output from processor 502. In this example, chipset 600 outputs information to output device 524, such as a display, and may read and write information to storage device 514, which may comprise, for example, magnetic media, and solid-state media. Chipset 600 may also read data from and write data to RAM 510. Bridge 602 for interfacing with a variety of user interface components 604 may be provided for interfacing with chipset 600. User interface components 604 may comprise a keyboard, a microphone, touch detection and processing circuitry, a pointing device, such as a mouse, and so on. In general, inputs to information handling system 146 may come from any of a variety of sources, machine generated and/or human generated.

Chipset 600 may also interface with one or more communication interfaces 526 that may have different physical interfaces. Such communication interfaces may comprise interfaces for wired and wireless local area networks, for broadband wireless networks, as well as personal area networks. Some applications of the methods for generating, displaying, and using the GUI disclosed herein may comprise receiving ordered datasets over the physical interface or be generated by the machine itself by processor 502 analyzing data stored in storage device 514 or RAM 510. Further, information handling system 146 receives inputs from a user via user interface components 604 and executes appropriate functions, such as browsing functions by interpreting these inputs using processor 502.

In examples, information handling system 146 may also comprise tangible and/or non-transitory computer-readable storage devices for carrying or having computer-executable instructions or data structures stored thereon. Such tangible computer-readable storage devices may be any available device that may be accessed by a general purpose or special purpose computer, including the functional design of any special purpose processor as described above. By way of example, and not limitation, such tangible computer-readable devices may comprise RAM, ROM, EEPROM, CD-ROM or other optical disk storage, magnetic disk storage or other magnetic storage devices, or any other device which may be used to carry or store desired program code in the form of computer-executable instructions, data structures, or processor chip design. When information or instructions are provided via a network, or another communications connection (either hardwired, wireless, or combination thereof), to a computer, the computer properly views the connection as a computer-readable medium. Thus, any such connection is properly termed a computer-readable medium. Combinations of the above should also be comprised within the scope of the computer-readable storage devices.

Computer-executable instructions comprise, for example, instructions and data which cause a general-purpose computer, special purpose computer, or special purpose processing device to perform a certain function or group of functions. Computer-executable instructions also comprise program modules that are executed by computers in stand-alone or network environments. Generally, program modules comprise routines, programs, components, data structures, objects, and the functions inherent in the design of special-purpose processors, etc., that perform particular tasks or implement particular abstract data types. Computer-executable instructions, associated data structures, and program modules represent examples of the program code means for executing steps of the methods disclosed herein. The particular sequence of such executable instructions or associated data structures represents examples of corresponding acts for implementing the functions described in such steps.

In additional examples, methods may be practiced in network computing environments with many types of computer system configurations, including personal computers, hand-held devices, multi-processor systems, microprocessor-based or programmable consumer electronics, network PCs, minicomputers, mainframe computers, and the like. Examples may also be practiced in distributed computing environments where tasks are performed by local and remote processing devices that are linked (either by hardwired links, wireless links, or by a combination thereof) through a communications network. In a distributed computing environment, program modules may be located in both local and remote memory storage devices.

During calibration of a gas chromatograph or during use of a calibrated gas chromatograph in accordance with the present disclosure, information handling system 146 may process different types of the real-time data and post-process data originated from varied sampling rates and various sources, such as diagnostics data, sensor measurements, gas chromatograph detector measurements, pressure/flow measurements, operations data, and or the like as collected by drilling system 100, gas extraction system 200, and/or gas extraction and chromatography system 300. (e.g., referring to FIGS. 1-3). These measurements (m) from drilling system 100 may allow for information handling system 146 to perform real-time assessments of the drilling system 100 gas extraction system 200, and/or gas extraction and chromatography system 300.

In addition to performing real-time analysis of a gas of drilling system 100, the methods and systems described herein may be configured to perform calibration of one or more gas chromatographs. While calibration of a gas chromatograph is generally shown as occurring in real-time during operation of drilling system 100 (e.g., referring to FIG. 1), it should be understood that the drilling fluid samples or sample gas may be stored and carried off site to another location where gas extraction, analysis, and subsequent calibration of gas chromatograph 500 may be performed.

FIG. 7 is a workflow 700 for calibrating a gas chromatograph according to one or more examples of the present disclosure. Operations of workflow 700 may be performed in real-time by information handling system 146.

In block 702, a drilling fluid sample 301 (e.g., referring to FIG. 3) is received from a flow of drilling fluid returning to the surface of a borehole during drilling of the borehole in a subterranean formation. For example, the drilling fluid sample may be received from one or more access points within a drilling fluid circulation system 100 (e.g., referring to FIG. 1).

In block 704, the drilling fluid sample 301 is optionally captured in a vessel that minimizes dissolved formational gas loss. For example, with reference to FIG. 3, the extraction system 302 outputs the drilling fluid sample for storage in vessel 304 that is pressure sealed to minimize loss of dissolved gas. The dissolved gas is later measured with a gas chromatograph.

In block 706, the drilling fluid sample is circulated and recirculated through the gas extractor to extract dissolved gas. For example, with reference to FIG. 3, the gas extraction system 302 receives the drilling fluid sample back from vessel 304 to be recirculated through the gas extraction system 302 to extract dissolved gas from the drilling fluid sample. In alternative examples, extracted dissolved gas proceeds directly to gas chromatograph 400 without being recirculated via vessel 304, or proceeds directly from vessel 304 to gas chromatograph 400.

In block 708, extracted dissolved gas is input into a gas chromatograph. For example, with reference to FIG. 3, the gas extraction system 302 inputs the extracted dissolved gas into gas chromatograph 400. Gas may be input directly into gas chromatograph 400 or may be diluted with, combined with, or added to both a carrier gas and/or diluent from diluent source 400. One or more components (e.g., analytes) of the extracted dissolved gas are at least partially separated by flowing carrier fluid and the gas through one or more chromatographic columns. The separated components are then detected using one or more detectors.

In block 710, concentration of one or more chemical species of the extracted dissolved gas are determined using the gas chromatograph over time. Specifically, data from the one or more detectors is produced. Data may comprise, for example, one or more response signals corresponding to one or more analytes over a range of concentrations. This data may later be used to render, for example, concentration versus time curves, response curves, area vs. concentration, etc. Data may alternatively, or additionally, comprise area and/or concentration of the various analytes, as well as ratios between concentrations.

In block 712, the data obtained in block 710 is assessed for linearity/non-linearity, and based on the linearity or non-linearity, recalibrating of the gas chromatograph 400 may be performed in block 714.

The "linear ratio test(s)," also referred to herein as "linearity test(s)" is/are done to confirm that the instrument readings are accurate across multiple orders of magnitude of concentration. These tests may define how and where an instrument lacks linearity by deviation of ratios. In some examples, the performing of the linear ratio test(s) may yield linearity data used to predict correction factors, which may then be used to generate new response curves or otherwise correct the output data of the gas chromatograph 400. Where performed correctly, this results in more accurate measurements for multi-component sample gases than what would be achieved using basic, low resolution response curves.

An example procedure for performing a linear ratio test is provided. A vessel is purged with a known concentration of a chemical or chemicals of interest. The vessel is then connected to a pump that is connected to a gas chromatograph. The pressure and flow rate of the output of the pump is controlled, and the gas chromatograph is calibrated at least at the initial concentration. The vessel is also opened to atmosphere or a non-interfering gas through a constrained port. The pump is turned on, and the sample in the vessel is moved to the gas chromatograph. Dilution occurs naturally (and/or artificially in the case of a diluter/diffuser) in the vessel as the sample is removed from the vessel, causing the gas concentration to fall within the vessel. The changing concentrations are captured as a function of time and the ratios are also determined as a function of time. The initial ratio is then used as a constraint to adjust the concentration factors to address the non-linearity of the response to area and to obtain correct concentrations. The adjusted factors are then fitted with the appropriate function(s) to get more accurate concentrations. The end goal is to get correct concentrations which may then be used to determine oil, gas, water, and other parameters of the formational fluids.

Linearity and non-linearity of a dataset may be determined in other ways as well, for example, various statistical tests, e.g., residual analysis, goodness-of-fit tests, derivative analysis, etc. Deviation of the linear ratios, e.g., from a projected linear trend, may be characterized using these and other techniques. Specific advantages of determining non-linearity using linear ratios (e.g., normalizing multi-component concentrations to a single species).

In block 714, based on the processed data and measurements of the one or more detectors, the gas chromatograph is recalibrated. This may comprise, for example, forming a second calibration forming wherein the second calibration is more accurate than a first (basic) calibration setting.

Figures 9, 10:
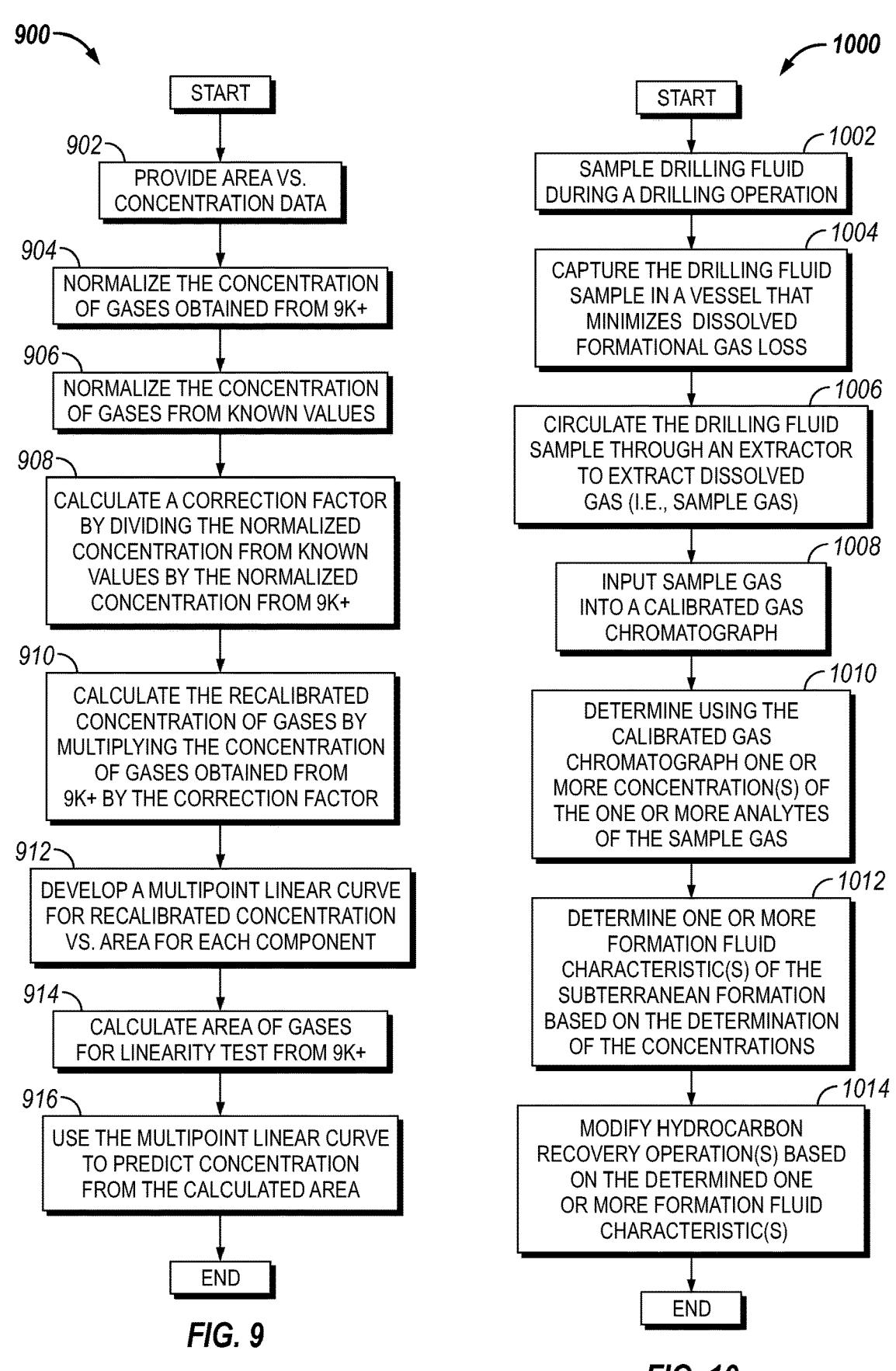
FIG. 9 illustrates a workflow for performing data processing during calibration of a gas chromatograph according to one or more examples of the present disclosure.
FIG. 10 illustrates a workflow depicting operations for using a calibrated gas chromatograph during a drilling operation according to one or more examples of the present disclosure.

As mentioned, data processing in block 712 may be performed in a variety of ways. To that end, FIGS. 8 and 9 provide examples for how data processing in block 712 may be performed.

FIG. 8 is a workflow 800 for performing data processing in block 712 (e.g., referring to FIG. 7). In examples, area vs. concentration data is provided. The "area" of a chromatograph in this context is the area under a peak of a response curve, which corresponds to a specific analyte and is proportional to the quantity of that analyte in a gas being tested by a gas chromatograph, and the "concentration" is the quantity of the analyte, usually expressed in moles or mass per volume.

As mentioned, workflow 800 of FIG. 8 may assume that area vs. concentration data is known. In alternative examples (e.g., referring to FIG. 9), area vs. concentration data may not be known, or a scenario may require calibration of a gas chromatograph without this information. For example, calibration of one or more gas chromatographs may need to be performed using other data. In this context, the "other data" may comprise, for example, calculated area or peak intensity. The operations of workflow 800 begin in block 802. As with workflow 700, the operations of workflow 800 may be performed by information handling system 146.

From block 802 to block 810, data (e.g., data obtained in block 712 of FIG. 7) is recalibrated. Data to be recalibrated in blocks 802-810 may comprise first linearity data. In this context, "first linearity data" refers to the concentration and area responses of a gas chromatograph using an initial, low resolution response curve, i.e., basic calibration. Essentially, the first linearity data is a dataset of nominal or guess values to be used as a starting point for a more accurate dataset and provides the basis for later correcting and fitting of calibration factors. In blocks 812 through 816, concentrations of one or more future linearity tests are calculated.

In block 802, a first dataset (i.e., the first linearity data) comprising concentration of gases obtained from a gas chromatograph (e.g., 9K+) is provided, as mentioned.

In block 804, the first dataset from block 802 is normalized to calculate a first normalized concentration. The first normalized concentration may be, for example, a singular value statistically representative of the entire dataset, and may be determined using various, well-known statistical normalization techniques. In alternative examples, the first normalized concentration may comprise a dataset of normalized concentrations having a reduced size (i.e., relative to the first dataset of block 802), and which is similarly determined using standard statistical normalization techniques.

In block 806, a second dataset comprising known concentrations of gases (e.g., predetermined or obtained from a calibration bottle) is also normalized to calculate a second normalized concentration. In this context, the second normalized concentration may be a singular value, or a dataset of values, statistically representative of the concentrations of one or more species present within a calibration gas.

In block 808, a correction factor is calculated from the first and second normalized concentrations (e.g., by dividing the second normalized concentration by the first normalized concentration). In examples where the first and second normalized concentrations of blocks 804 and/or 806 comprise non-singular data, the correction factor may likewise comprise a dataset of correction factors. In such examples, the size of the dataset may correspond or be equal to either or both the first and second normalized concentrations.

In block 810, each datapoint in the first dataset of block 802 is multiplied by the correction factor(s) to form a corrected dataset, and a multipoint linear curve is developed from the corrected dataset. The corrected dataset in this context may comprise, for example, a recalibrated concentration versus area curve for each component of the gas.

In block 812, concentration ratios of methane with respect to other gases from linearity test data are calculated.

In block 814, the multipoint linear curve of block 810 is used to predict one or more correction factors based on the one or more concentration ratios calculated in block 812. It should be noted that the predicted correction factors may be an array of values spanning a range of concentrations, and which may be predicted using linear regression, curve-fitting, model-fitting, or equivalent techniques. Predicting of correction factors may, in some examples, involve interpolating and/or extrapolating of the multipoint linear curve of block 810. Use in this manner effectively allows the complex relationships between the various components of a sample gas and the response signal to be accounted for, thereby capturing any non-linearities in the output.

In block 816, a recalibrated dataset is produced by multiplying one or more concentrations of the first dataset from block 802 by the predicted correction factors of block 814. When performed correctly, the recalibrated dataset of block 816 is more accurate than the first dataset of block 802.

FIG. 9 is a workflow 900 for performing data processing in block 712 (e.g., referring to FIG. 7) when only concentrations from one or more linearity tests are known. As used in this context, concentrations from the one or more linearity tests are known when, for example, only the initial concentrations and concentration ratios are known. More particularly, workflow 900 may be used in scenarios where area vs. concentration data, i.e., from a gas chromatograph, is not known.

The operations of workflow 900 begin in block 902. As with previous workflows, operations of workflow 900 may be performed by information handling system 146. From block 904 to block 914, data of the first linearity data is recalibrated. From blocks 916 through 918, concentrations of one or more future linearity tests are calculated.

In block 902, area vs. concentration data is provided. This data may be obtained by calculating ratios of the concentration of methane with respect to other gas components in a gas.

In block 904, a first data set (not to be confused with the "first data set" of block 804) comprising gas concentrations obtained from 9 k+ is normalized to calculate a first normalized concentration.

In block 906, a second data set (not to be confused with the "second data set" of block 806) comprising known gas concentrations (e.g., from a calibration bottle) is also normalized to calculate a second normalized concentration.

In block 908, the correction factor(s) is/are determined using the first and second normalized concentrations of blocks 904 and 906 (e.g., by dividing the first normalized concentration by the second normalized concentration).

In block 910, the recalibrated concentrations of gases are calculated using the correction factor(s) and the first dataset of block 902 (e.g., by multiplying the first data set by the correction factor).

In block 912, a multipoint linear curve is developed which represents a recalibrated correction factor vs ratio for each component. In one or more examples, the ratio having the highest deviation from an actual calibration bottle ratio may be used for methane.

In block 914, ratios of the concentration of methane with respect to other gas components are calculated from linearity test data from 9 k+.

In block 916, the multipoint linear curve developed in block 916 is used to predict correction factor based on the calculated ratios, and each data point of the first data set (e.g., referring to block 906) is multiplied by the predicted correction factor to produce a corrected dataset. The corrected dataset may, in some examples, be more accurate than the first dataset.

As alluded to previously, gas extraction and chromatography system 300 (e.g., referring to FIG. 3) may be used to perform one or more blocks of workflows 700, 800, and/or

900 at drilling system 100 (e.g., referring to FIG. 1) or at an offsite location. One or more calibrated gas chromatographs may be incorporated into and/or used alongside drilling system 100. Accordingly, FIG. 10 illustrates how a calibrated gas chromatograph may be used in such an environment. It should be understood that, while workflow 1000 is discussed with reference to drilling systems, the calibrated gas chromatograph of the present disclosure should not be limited only to drilling systems.

FIG. 10 is a workflow 1000 for using a calibrated gas chromatograph during a drilling operation according to one or more examples of the present disclosure. As with FIGS. 6-9, one or more operations of FIG. 10 may be performed by information handling system 146.

In block 1002, recirculated drilling fluid of a borehole extending into a subterranean formation during a drilling operation is sampled. The drilling fluid sample comprises one or more analytes. A drilling operation may proceed in the manner previously described for drilling system 100 (e.g., referring to FIG. 1). Block 1002 may alternatively comprise any suitable oil and gas operation at a well site such as, for example, logging, well testing, completion, casing and cementing, hydraulic fracturing, production, well stimulation, or any other operation where it is desired to estimate formation fluid properties.

In block 1004, the drilling fluid sample is optionally captured in a vessel that minimizes dissolved formational gas loss. The arrangement of FIG. 3 which shows sample gas being recirculated between a vessel 304 and gas extraction system 302 may allow larger sample sizes as well as reduced formational gas loss. In alternative examples, sample gas may bypass vessel 304 and proceed directly towards gas chromatograph 400. It should be understood that while not shown, one or more pumps, circulators, flow control devices, etc., or any suitable device for facilitating proper functioning of gas extraction and chromatography system 300 may be included to carry out the operations of block 1004.

In block 1006, the drilling fluid sample is circulated through a gas extractor to extract dissolved gas. Extraction of the dissolved gas may involve the use of one or more fans, pumps, permeable medium, gas detectors/monitors, bags, canisters, scrubbers, filters, vacuum pumps, probes, samplers (e.g., autosamplers), combinations thereof, or the like. The extracted dissolved gas comprises the one or more analytes and may be predominantly or completely comprised of chemical components in the vapor phase.

In block 1008, one or more gases comprising sample gas is input into a calibrated gas chromatograph. The calibrated gas chromatograph generally comprises one or more columns, one or more detectors, and a stationary phase. In operation, a mobile phase, i.e., carrier gas, carries the one or more analytes through the stationary phase of the gas chromatograph. The one or more analytes are at least partially separated (e.g., from each other, non-analyte(s), and/or inert compounds) as they pass through the one or more columns, and the at least partially separated analytes are then analyzed using one or more detectors of the gas chromatograph. One or more temperature controllers may regulate the temperature of the gas as it flows through the gas chromatograph. Other devices may, in some examples, be included within a calibrated gas chromatograph, such as one or more pressure controllers to control the pressure (e.g., at either side of the one or more chromatographic columns), one or more pressure/flow gauges (e.g., for monitoring flow), one or more column ovens/heaters, a data system and/or software (e.g., for acquiring and/or storing response signals of the one or more detectors and transmitting them to information handling system 146), a waste collector for disposing of analyzed gas, combinations thereof, and the like. The calibrated gas chromatograph may be calibrated according to one or more blocks of workflow 700 (e.g., referring to FIG. 6), and may be operable to determine concentrations of analytes based at least in part on one or more complete response curves.

In block 1010, the calibrated gas chromatograph is used to determine one or more concentrations of the one or more analytes of the sample gas. Determining concentrations in block 1010 may comprise rendering a response signal versus time curve (e.g., chromatogram). Area under one or more regions of the curve (e.g., peaks) may be used to estimate the concentration of one or more analytes. Determining concentrations of one or more analytes may also involve the use of extrapolation and/or interpolation of the one or more response curves. In addition, or in the alternative, determining concentrations may involve the use of, for example, simple linear regression, multiple linear regression, polynomial regression, ridge regression (L2 regularization), lasso regression (L1 regularization), elastic net regression, Poisson regression, quantile regression, generalized additive models (GAM).

In block 1012, one or more formation fluid characteristics of the subterranean formation are determined based on the determined concentrations of the gas. For example, with reference to FIG. 3, information handling system 146 can determine a formation characteristic based on the determined values of concentration of one or more analytes of the sample gas. Determining the formation characteristic using the determined chemical composition may comprise comparing the determined chemical composition to known chemical compositions of subterranean formations. The formation characteristics may comprise at least one of a type of rock in the subterranean formation, the presence of hydrocarbons in the subterranean formation, the production potential for a stratum of the subterranean formation, and the movement of fluid within the strata. Determination of one or more concentrations of the one or more analytes of the sample gas may yield analyte concentration and response signal data which may be used to estimate one or more properties, analyte concentrations, or other material factor associated with reservoir fluid. Non-limiting examples of formation fluid properties which may be estimated by the determination of analyte(s) in block 1010 may include chemical composition, gas-to-oil ratio (GOR), molecular weight, density, formation volume factor (FVF), specific gravity, heating value (i.e., calorific value), viscosity, Wobbe index, combinations thereof, and the like.

Estimating of concentrations of analyte(s) in a formation fluid or other properties may be performed in any suitable manner including, without limitation, linear regression methods, curve-fitting, extrapolation, interpolation, and the like, as well as non-graphical methods such as with "black box" methods including, for example, machine learning and/or artificially intelligent algorithms. Exemplary machine learning and/or artificially intelligent algorithms to be used in in a black box model may include, without limitation, a supervised, semi-supervised, unsupervised, and/or reinforced model, a binary classification model, a multiclass classification model, a regression models, decision trees, a random forest classifier, logistic regression, support vector machine algorithms (SVM), a Naive Bayes classifier, k-nearest neighbors (K-NN) algorithms, clustering, k-means clustering, a dimensionality reduction algorithm, a gradient boosting algorithm, a probabilistic classifier, the like, and any combination thereof.

In block 1014, hydrocarbon recovery operation(s) is modified based on the determined formation fluid characteristic(s). For example, the current drilling operation could be modified (e.g., direction, rate, pills, etc.).

Thus, in contrast to conventional approaches, the present disclosure may provide improved methods and systems for calibrating gas chromatographs. Gas chromatography response curves produced by these methods and systems may be both more accurate as well as better representative of the relationships between a gas chromatograph's response signal and the concentration of one or more analytes in a gas. In addition, gas chromatographs calibrated using the methods disclosed herein may produce more accurate estimates or predictions of one or more analytes present within drilling fluids, formation fluids, or other wellbore fluids or extracted samples.

Accordingly, the present disclosure may provide methods for calibrating gas chromatographs as well as performing well site operations using improved chromatography. The methods and systems may include any of the various features disclosed herein, including one or more of the following statements.

Statement 1: A method comprising: varying at least a concentration of one or more components of a multi-component sample gas across at least a concentration range while introducing the multi-component sample gas into a gas chromatograph comprising one or more chromatographic columns; measuring concentrations of the one or more components with the gas chromatograph at a first calibration setting; determining one or more non-linearities of the measured concentrations at the first calibration setting; forming a second calibration setting based at least in part on the one or more non-linearities; and measuring concentrations of one or more components of another sample gas with the gas chromatograph at the second calibration setting.

Statement 2: The method of statement 1, wherein concentrations of at least two of the components of the multi-component sample gas are increased or decreased during introducing of the multi-component sample gas into the gas chromatograph.

Statement 3: The method of statement 2, wherein the varying of the concentrations occurs continuously by at least one technique selected from the group consisting of a continuous top purge, a continuous bottom purge, automated dilution, and any combination thereof.

Statement 4: The method of any of statements 1-3, further comprising determining one or more correction factors based on the one or more non-linearities.

Statement 5: The method of statement 4, further comprising predicting one or more additional correction factors from the one or more correction factors, wherein the second calibration factor is based, at least in part, on the predicted one or more additional correction factors.

Statement 6: The method of statement 5, wherein the one or more additional correction factors are predicted by: fitting one or more curves to the one or more correction factors; and interpolating and/or extrapolating the one or more curves to produce the one or more additional correction factors.

Statement 7: The method of any of statements 1-6, further comprising forming a multilinear curve of some or all of the measured components of the multi-component sample gas.

Statement 8: The method of any of statements 1-7, further comprising calculating linear ratios of some or all of the components of the multi-component sample gas with respect to at least one of the components of the multi-component sample gas.

Statement 9: The method of statement 8, wherein the determining of the one or more non-linearities is based at least in part on deviation of the linear ratios from a projected linear trend.

Statement 10: The method of any of statements 1-9, wherein: the determining of the one or more non-linearities is performed using an information handling system; the multi-component sample gas comprises five or more species; and the forming of the second calibration setting is performed using five measurement points or less.

Statement 11: The method of any of statements 1-10, further comprising: sampling a wellbore fluid during a wellbore operation; and extracting one or more gases from the wellbore fluid, wherein the additional sample gas comprises the one or more extracted gases, and wherein the measuring of the concentrations of the one or more components of the additional sample gas at the second calibration setting is performed using an information handling system communicatively coupled to the gas chromatograph.

Statement 12: A method comprising: extracting a multi-component sample gas from a wellbore fluid; and measuring concentrations of one or more components of the multi-component sample gas with a gas chromatograph, the gas chromatograph having a calibration setting, wherein the calibration setting corrects for one or more non-linearities of a previous calibration setting, wherein the calibration setting represents results of one or more linear ratio tests.

Statement 13: The method of statement 12, further comprising assessing linearity or non-linearity by comparing one or more linear ratios to a projected linear trend.

Statement 14: The method of statement 13, wherein the calibration setting comprises: a plurality of correction factors derived from the one or more linear ratio tests; and one or more predicted correction factors derived from the plurality of correction factors.

Statement 15: The method of any of statements 12-14, wherein the calibration data is based at least in part on a measured response of a partially calibrated gas chromatograph varying at least a concentration of one or more components of a first multi-component sample gas across at least a concentration range while introducing the multi-component sample gas into a gas chromatograph comprising one or more chromatographic columns.

Statement 16: The method of any of statements 12-15 wherein the calibration data is based at least in part on varying concentrations continuously by at least one technique selected from the group consisting of a continuous top purge, a continuous bottom purge, automated dilution, and any combination thereof.

Statement 17: A system comprising: a wellbore extending into a subterranean formation; a gas chromatograph configured to measure concentrations of one or more components of a multi-component sample gas at a calibration setting; and an information handling system communicatively coupled to the gas chromatograph, wherein the calibration setting accounts for one or more non-linearities of the measured concentrations based at least in part on calibration data, the calibration data representing one or more results of one or more linear ratio tests.

Statement 18: The system of statement 17, wherein the one or more linear ratio tests comprise: purging a vessel with a purge gas having a known concentration of at least a chemical of interest; connecting a pump to a gas chromatograph and the vessel; controlling pressure and flow rate of an output of the pump; calibrating the gas chromatograph at least at an initial concentration of the purge gas; opening the vessel to atmosphere or a non-interfering gas through a constrained port; activating the pump, wherein dilution occurs within at least the vessel; capturing one or more changes to concentrations of the at least a chemical of interest as a function of time; determining linear ratios as a function of time; adjusting a plurality of correction factors using the linear ratios as a constraint; and fitting the adjusted correction factors with one or more functions to obtain more accurate concentrations.

Statement 19: The system of statements 1 or 8, wherein the calibration setting comprises: a plurality of correction factors derived from the one or more linear ratio tests; and one or more predicted correction factors derived from the plurality of correction factors.

Statement 20: The system of statement 19, wherein the calibration data comprises one or more multi-linear curves associated with at least one compound selected from the group consisting of methane, ethane, propane, butane, isobutane, pentane, isopentane, and any combination thereof.

To facilitate a better understanding of the present invention, the following examples of certain aspects of some examples are given. In no way should the following examples be read to limit, or define, the entire scope of the disclosure.

EXAMPLES

FIGS. 11A-11G represent measurements of a sample gas by 8900 and 9250 gas chromatography systems. Measurement by these 8900 and 9250 systems were repeated for a sample gas after calibrating the gas chromatographs using various calibration techniques. The results shown by FIGS. 11A-11G show how concentration ratios of species do not hold constant when using gas chromatographs calibrated according to calibration techniques not involving the linear ratio test(s) of the present disclosure. Specifically, in juxtaposition to the results shown in FIGS. 11A-11G, the linear ratio test(s) of the present disclosure may allow a plot of the concentration ratios for a measured sample gas to exhibit less variation across the measurement range.

Parameters varied during the various calibrations used in FIGS. 11A-11G include size of the vessel, the use or non-use of a diffuser and baffle, type of purging, and the use or non-use of linear ratio testing during calibration. The size of the vessel was either small or large. The diffuser was used to vary the concentration of one or more of the analytes (e.g., methane, ethane, pentane, etc.) of some of the samples of the sample gas during calibration, and the baffle was used to ensure good mixing of the samples during dilution by the diffuser. Varying of the concentration(s) of the species of the sample gas with the diffuser entailed adding one or more components to the sample gas with a diffuser at a controlled rate. The type of purging was either a "continuous bottom purge," i.e., "bottom purge," or a "continuous top purge," i.e., "top purge." A continuous bottom purge was used to preferentially remove the heavier components (e.g., pentane, isopentane) from the sample gas during calibration, whereas the continuous top purge was used to preferentially remove the lighter components (e.g., ethane, propane, butane) from the sample gas during calibration.

In some examples, the gas chromatography systems were calibrated by either adding one or more components to the sample gas with a diffuser at a controlled rate (e.g., FIG.), by continuously removing lighter or heavier components from the sample gas (e.g., FIG.), or both while the sample gas was being introduced to the chromatographic column(s). Use in this way ensured an even distribution of species concentrations over time so as to allow the 8900 and 9250 systems to incrementally measure the sample gas across a wide range of concentration ratios.

For each of FIGS. 11A-11G, the x-axis is the concentration (ppm) of methane ("C1") in a gas, and the y-axis is are linear ratios of C1 with respect to C2, C3, nC4, iC4, C5, and iC5 as detected by the gas chromatograph. To perform the procedure, a vessel was purged with gas until the concentration of C1 reached an initial concentration between 97% and 99% of a high standard calibration gas. After the initial purge, the sample gas was added to the vessel at a controlled rate to vary the concentrations of the various components within the vessel, such that the concentration of methane decreased gradually across the 10000 ppm to 1000 ppm range.

Figure 11A:
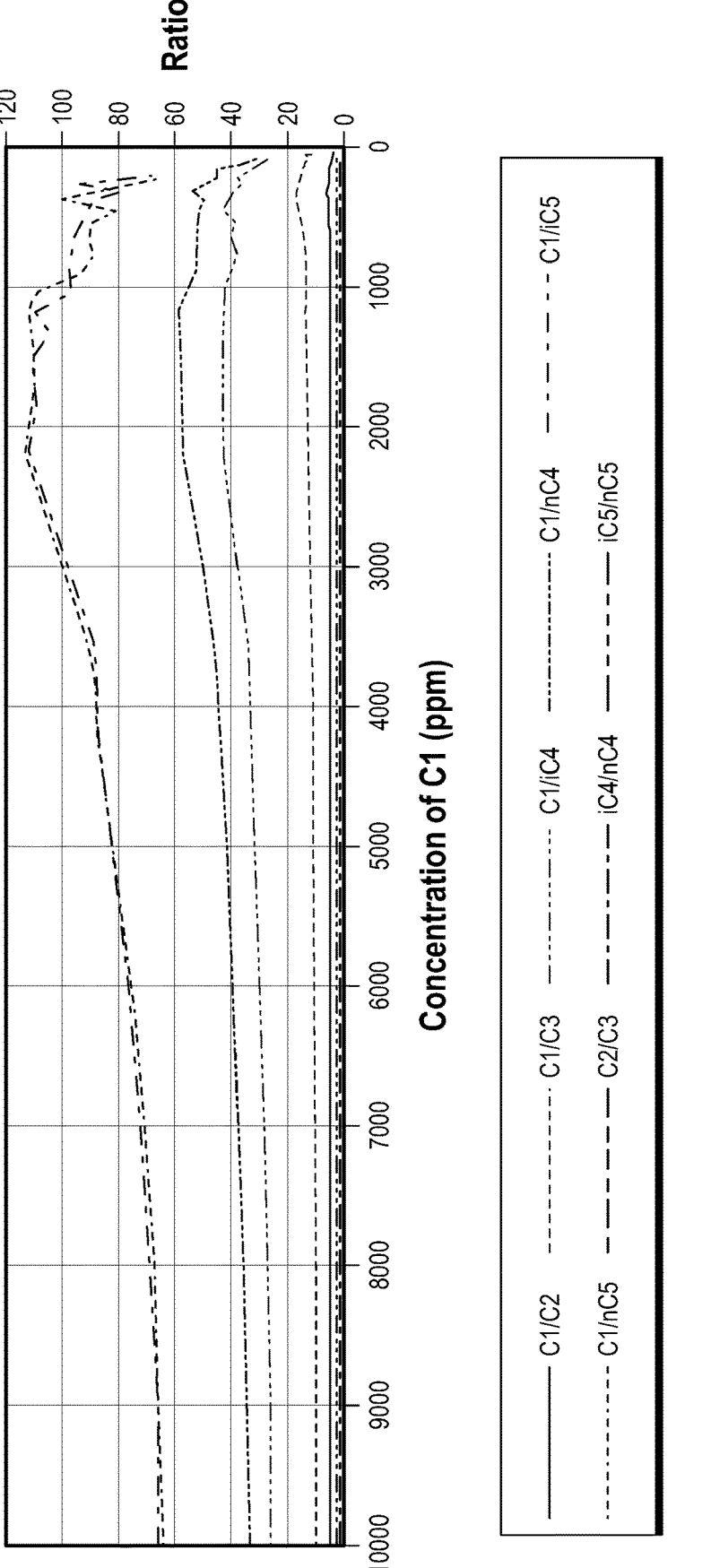
FIG. 11A is a plot showing results of a sample gas tested by a gas chromatograph calibrated with a multipoint calibration in 9K+ using a small vessel, without any linear ratio tests, diffuser, or baffle, but with a top purge.

FIG. 11A is a plot showing results of a sample gas tested by a gas chromatograph calibrated with a multipoint calibration in 9K+ using a small vessel, without any linear ratio tests, diffuser, or baffle, but with a top purge.

Figure 11B:
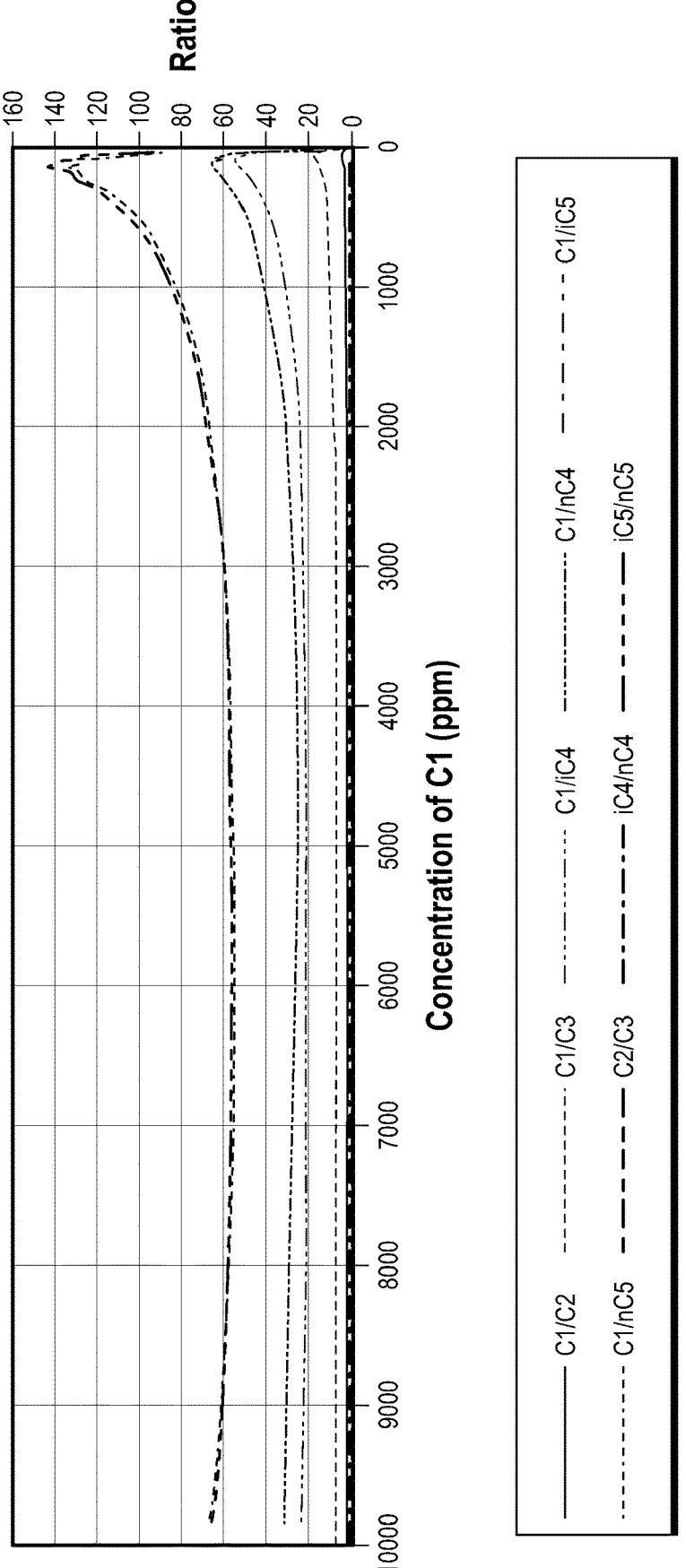
FIG. 11B is a plot showing results of a sample gas tested by a gas chromatograph calibrated in the same way as that for FIG. 11A, except that the vessel achieved a slightly higher concentration of a high standard calibration gas during the measurement period.

FIG. 11B is a plot showing results of a sample gas tested by a gas chromatograph calibrated in the same way as that for FIG. 11A, except that the vessel achieved a slightly higher concentration of a high standard calibration gas during the measurement period.

Figure 11C:
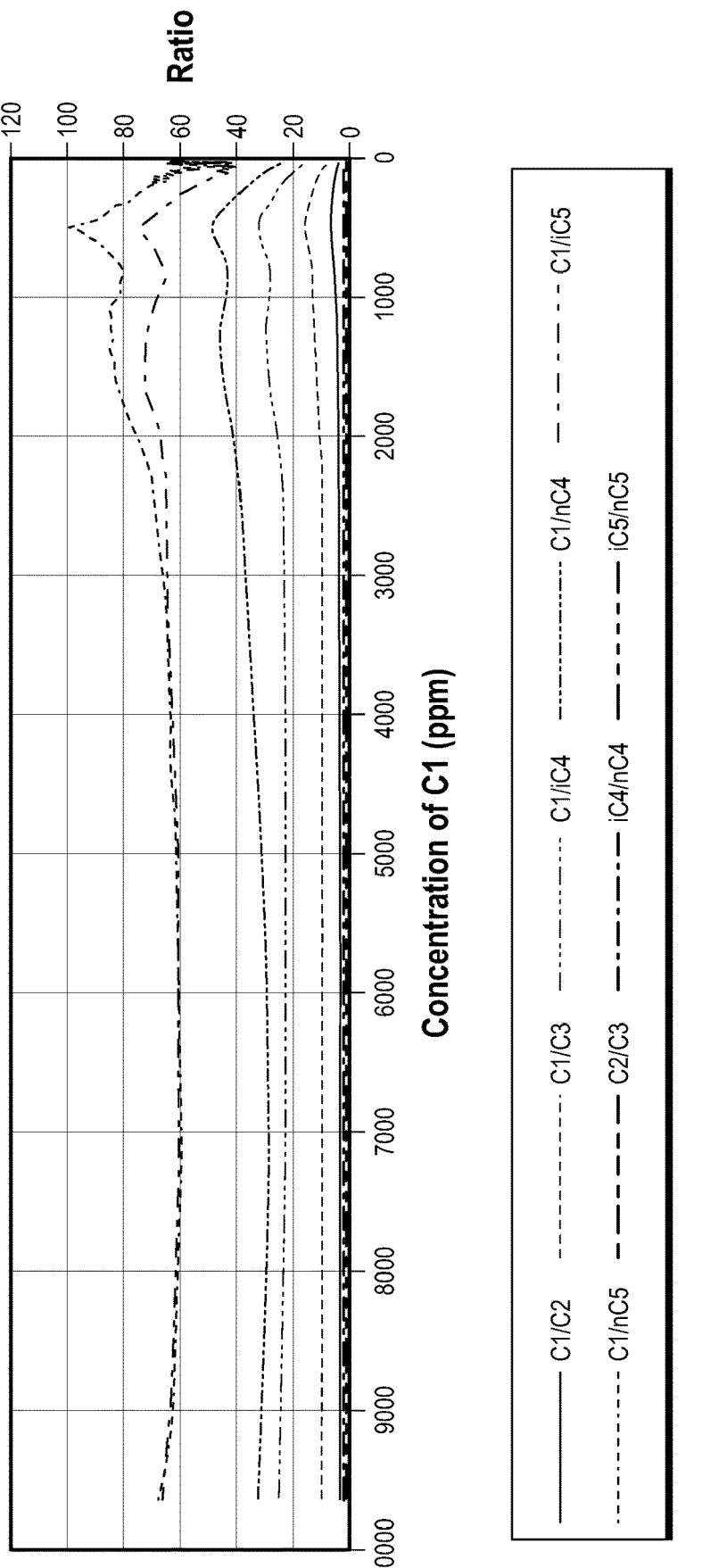
FIG. 11C is a plot showing results of a sample gas tested by a gas chromatograph calibrated in the same way as in FIG. 11A, except that the multipoint calibration was performed using 8900 rather than 9K+.

FIG. 11C is a plot showing results of a sample gas tested by a gas chromatograph calibrated in the same way as in FIG. 11A, except that the multipoint calibration was performed using 8900 rather than 9K+.

Figure 11D:
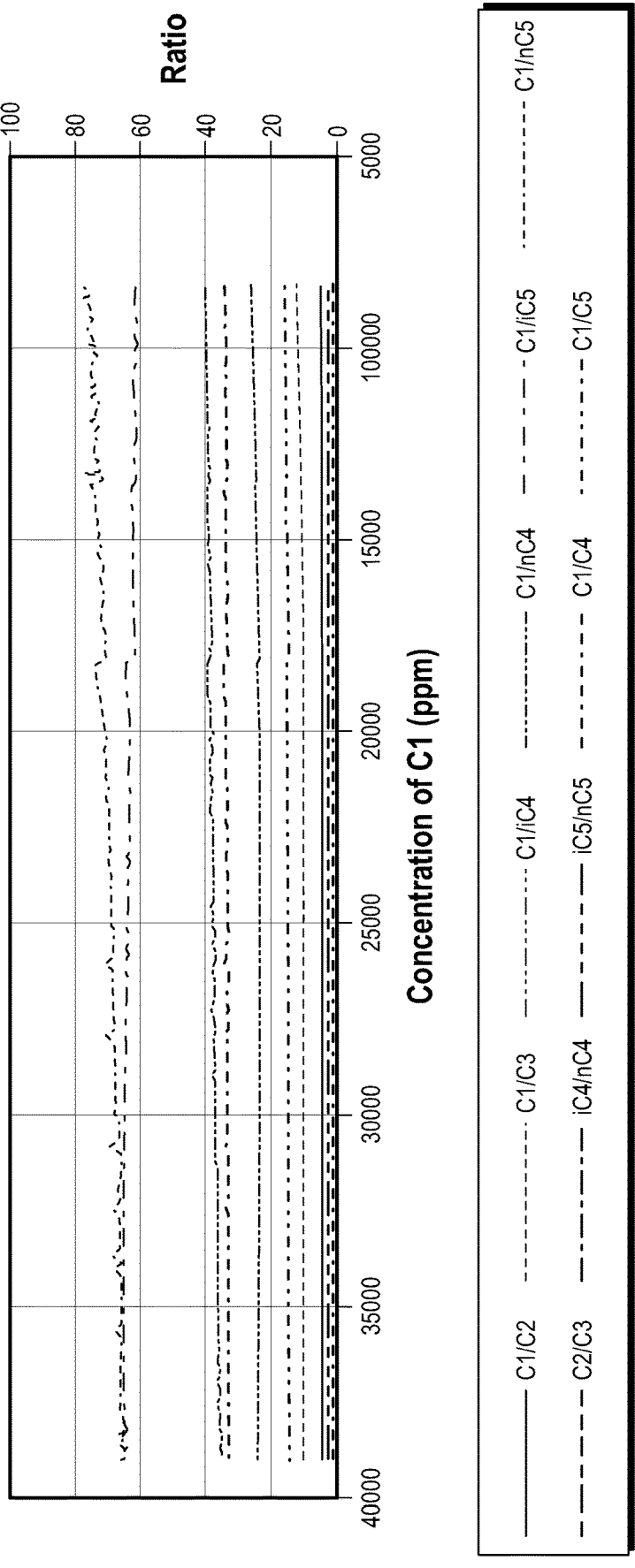
FIG. 11D is a plot showing results of a sample gas tested by a gas chromatograph calibrated in the same way as in FIG. 11C, except that a big vessel was used instead of a small vessel.

FIG. 11D is a plot showing results of a sample gas tested by a gas chromatograph calibrated in the same way as in FIG. 11C, except that a big vessel was used instead of a small vessel. It is observed that the ratios represented by FIG. 11D do not have the same "U curve" that appears when a small vessel is used. Without being limited by theory, it is believed that this lack of a U curve is attributed to poor mixing of the components within the vessel, which leads to dead space.

Figure 11E:
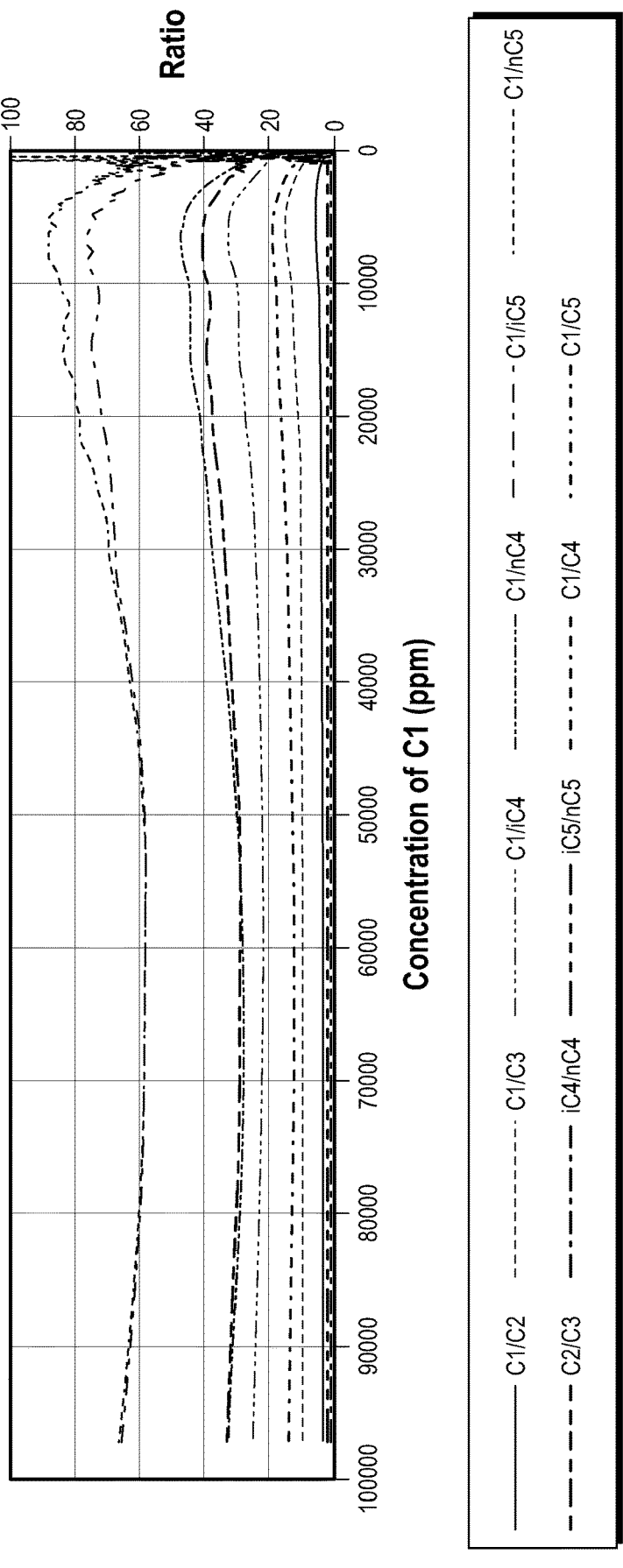
FIG. 11E is a plot showing results of a sample gas tested by a gas chromatograph calibrated in the same way as in FIG. 11C, except that a diffuser was attached to the gas chromatograph.

FIG. 11E is a plot showing results of a sample gas tested by a gas chromatograph calibrated in the same way as in FIG. 11C, except that a diffuser was attached to the gas chromatograph by a ¾ inch fitting.

Figure 11F:
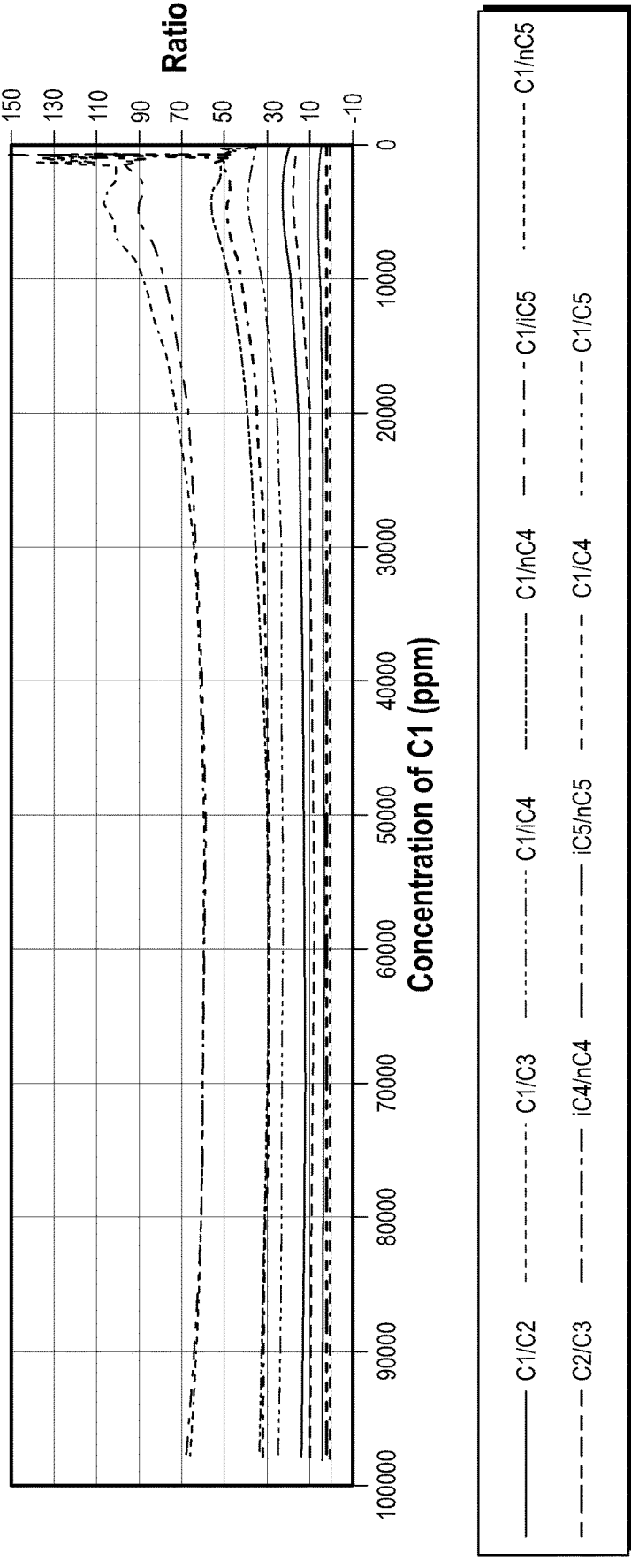
FIG. 11F is a plot showing results of a sample gas tested by a gas chromatograph calibrated in the same way as in FIG. 11E, except that structural packing was used a baffle and placed above the diffuser.

FIG. 11F is a plot showing results of a sample gas tested by a gas chromatograph calibrated in the same way as in FIG. 11E, except that structural packing was used a baffle and placed above the diffuser.

Figure 11G:
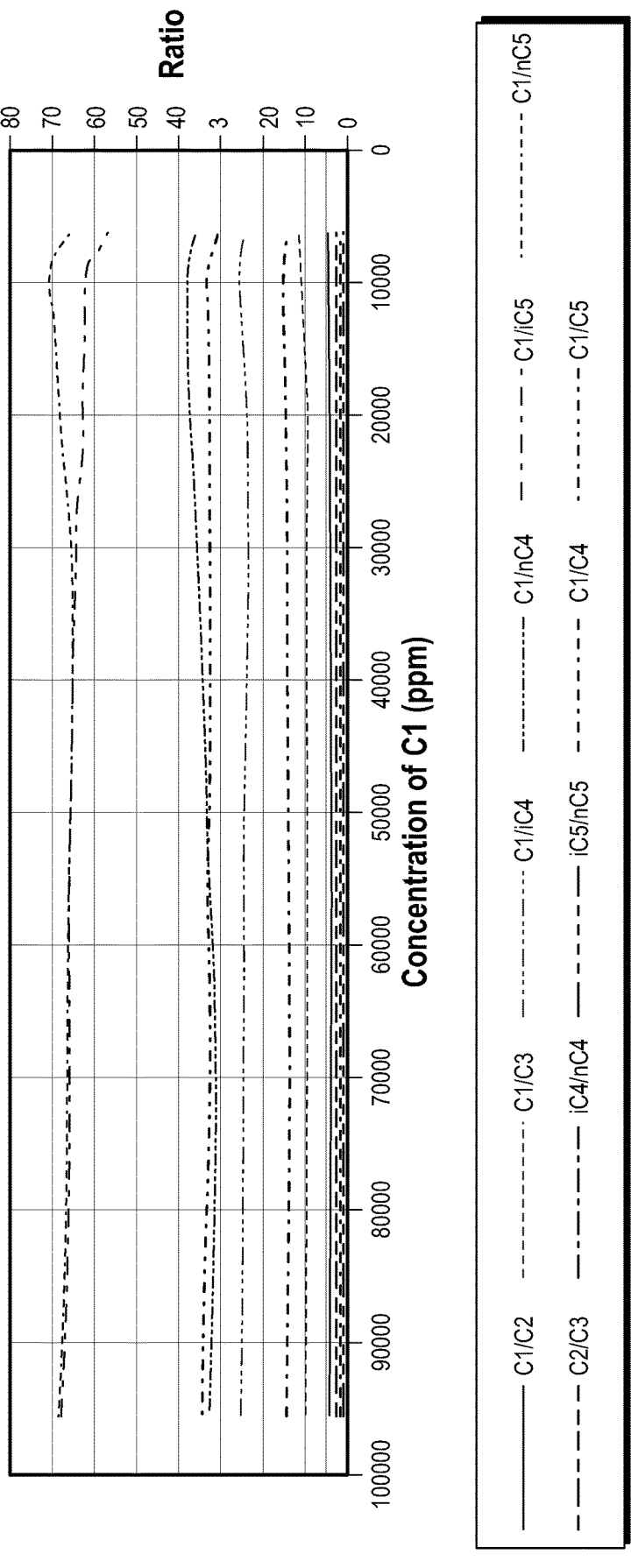
FIG. 11G is a plot showing results of the same procedure as in FIG. 11F, except that a bottom purge was used instead of a top purge.

FIG. 11G is a plot showing results of the same procedure as in FIG. 11F, except that a bottom purge was used instead of a top purge. Specifically, vacuum pressure was applied at the top and gas was inserted through a tube, where a pump was later changed on a deep tube, and where air was pulled through the top of the vessel.

Figure 12:
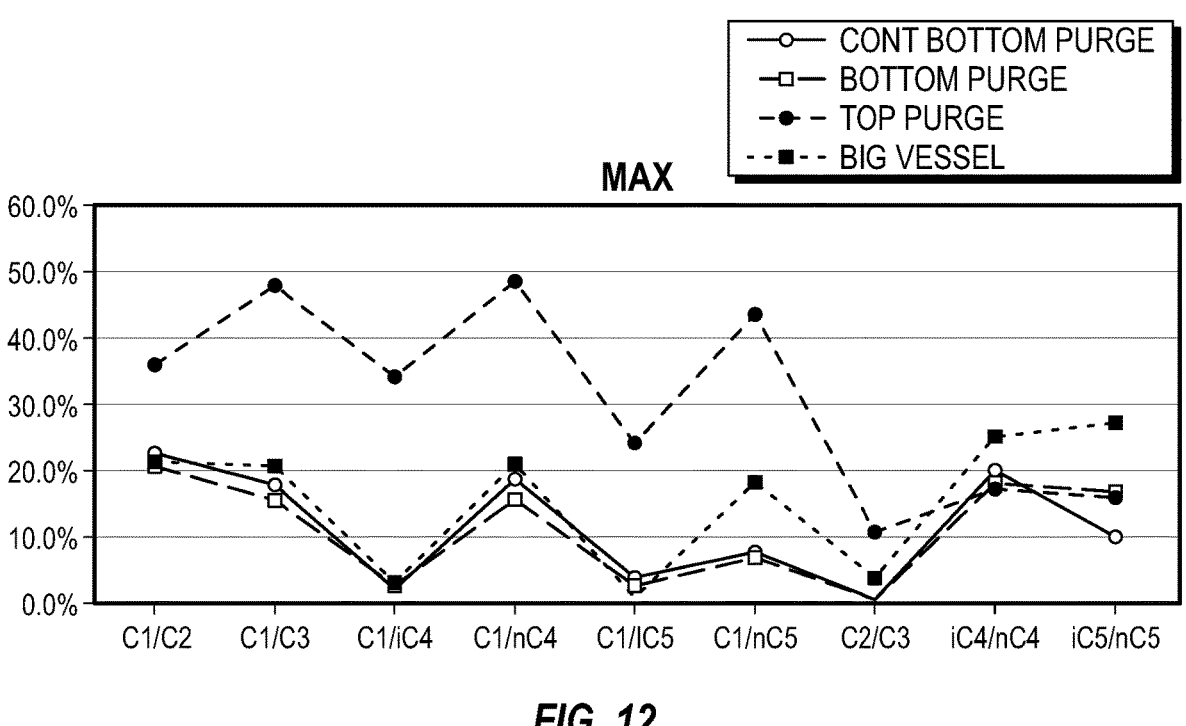
FIG. 12 is a plot showing a comparison of maximum methane-to-species ratios using various purging techniques according to one or more examples of the present disclosure.

FIG. 12 is a plot showing comparisons of maximum ratios of methane with respect to various $C_2$-$C_5$ components when gas calibration was performed with a continuous bottom purge (i.e., bottom purge), a top purge, and a big vessel, respectively. From left to right, the x-axis are the ratios: C1/C2, C1/C3, C1/iC4, C1/nC4, C1/iC5, C1/nC5, C2/C3, iC4/nC4, and iC5/nC5. The y-axis shows maximum ratio values.

Figure 13:
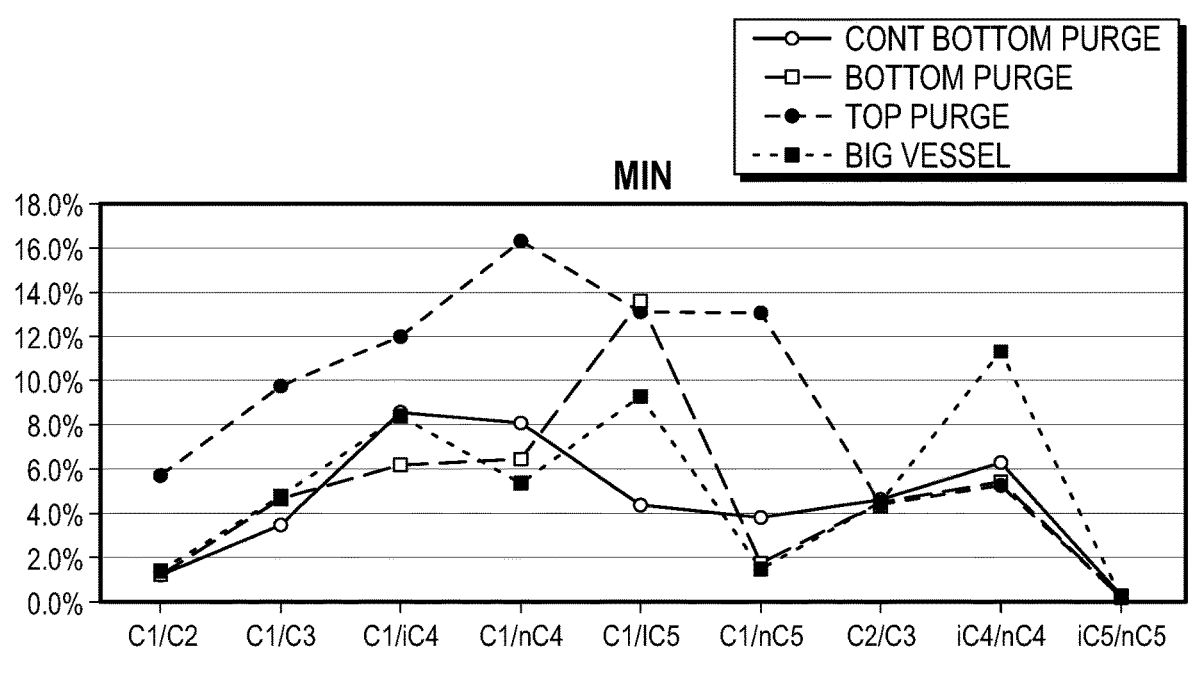
FIG. 13 is a plot showing minimum methane-to-species ratios using various purging techniques according to one or more examples of the present disclosure.

FIG. 13 is a plot showing comparisons of minimum ratios of methane with respect to various $C_2$-$C_5$ components when gas calibration was performed with a continuous bottom purge, a bottom purge, a top purge, and a big vessel, respectively. FIG. 13 is substantially similar to FIG. 12, except that minimum ratio values rather than maximum ratio values are provided.

Although specific examples have been described above, these examples are not intended to limit the scope of the present disclosure, even where only a single example is described with respect to a particular feature. Examples of features provided in the disclosure are intended to be illustrative rather than restrictive unless stated otherwise. The above description is intended to cover such alternatives, modifications, and equivalents as would be apparent to a person skilled in the art having the benefit of this disclosure.

The scope of the present disclosure includes any feature or combination of features disclosed herein (either explicitly or implicitly), or any generalization thereof, whether or not it mitigates any or all of the problems addressed herein. Various advantages of the present disclosure have been described herein, but examples may provide some, all, or none of such advantages, or may provide other advantages.

As used herein, the singular forms "a", "an", and "the" include singular and plural referents unless the content clearly dictates otherwise. Furthermore, the word "may" is used throughout this application in a permissive sense (i.e., having the potential to, being able to), not in a mandatory sense (i.e., must). The term "include," and derivations thereof, mean "including, but not limited to." The term "coupled" means directly or indirectly connected.

Therefore, the present examples are well adapted to attain the ends and advantages mentioned as well as those that are inherent therein. The particular examples disclosed above are illustrative only, as the present examples may be modified and practiced in different but equivalent manners apparent to those skilled in the art having the benefit of the teachings herein. Although individual examples are discussed, all combinations of one or more examples are contemplated and covered by the disclosure. Furthermore, no limitations are intended to the details of construction or design shown herein, other than as described in the claims below. Also, the terms in the claims have their plain, ordinary meaning unless otherwise explicitly and clearly defined by the patentee. It is therefore evident that the particular illustrative examples disclosed above may be altered or modified and all such variations are considered within the scope and spirit of the present disclosure.

What is claimed is:

1. A method comprising:

varying at least a concentration of one or more components of a multi-component sample gas across at least a concentration range while introducing the multi-component sample gas into a gas chromatograph comprising one or more chromatographic columns;

measuring concentrations of the one or more components with the gas chromatograph at a first calibration setting;

determining one or more non-linearities of the measured concentrations at the first calibration setting based at least in part on deviation of the linear ratios from a projected linear trend;

forming a second calibration setting based at least in part on the one or more non-linearities; and measuring concentrations of one or more components of another sample gas with the gas chromatograph at the second calibration setting.

2. The method of claim 1, wherein concentrations of at least two of the components of the multi-component sample gas are increased or decreased during introducing of the multi-component sample gas into the gas chromatograph.

3. The method of claim 2, wherein the varying of the concentrations occurs continuously by at least one technique selected from the group consisting of a continuous top purge, a continuous bottom purge, automated dilution, and any combination thereof.

4. The method of claim 1, further comprising determining one or more correction factors based on the one or more non-linearities.

5. The method of claim 4, further comprising predicting one or more additional correction factors from the one or more correction factors, wherein the second calibration factor is based, at least in part, on the predicted one or more additional correction factors.

6. The method of claim 5, wherein the one or more additional correction factors are predicted by:

fitting one or more curves to the one or more correction factors; and interpolating and/or extrapolating the one or more curves to produce the one or more additional correction factors.

7. The method of claim 1, further comprising forming a multilinear curve of some or all of the measured components of the multi-component sample gas.

8. The method of claim 1, further comprising calculating linear ratios of some or all of the components of the multi-component sample gas with respect to at least one of the components of the multi-component sample gas.

9. The method of claim 1, wherein:

the determining of the one or more non-linearities is performed using an information handling system;

the multi-component sample gas comprises five or more species; and the forming of the second calibration setting is performed using five measurement points or less.

10. The method of claim 1, further comprising:

sampling a wellbore fluid during a wellbore operation; and extracting one or more gases from the wellbore fluid, wherein the additional sample gas comprises the one or more extracted gases, and wherein the measuring of the concentrations of the one or more components of the additional sample gas at the second calibration setting is performed using an information handling system communicatively coupled to the gas chromatograph.

11. A method comprising:

extracting a multi-component sample gas from a wellbore fluid; and measuring concentrations of one or more components of the multi-component sample gas with a gas chromatograph, the gas chromatograph having a calibration setting, wherein the calibration setting corrects for one or more non-linearities of a previous calibration setting, wherein the calibration setting represents results of one or more linear ratio tests.

12. The method of claim 11, further comprising assessing linearity or non-linearity by comparing one or more linear ratios to a projected linear trend.

13. The method of claim 12, wherein the calibration setting comprises:

a plurality of correction factors derived from the one or more linear ratio tests; and one or more predicted correction factors derived from the plurality of correction factors.

14. The method of claim 11, wherein the calibration data is based at least in part on a measured response of a partially calibrated gas chromatograph varying at least a concentration of one or more components of a first multi-component sample gas across at least a concentration range while introducing the multi-component sample gas into a gas chromatograph comprising one or more chromatographic columns.

15. The method of claim 11, wherein the calibration data is based at least in part on varying concentrations continuously by at least one technique selected from the group consisting of a continuous top purge, a continuous bottom purge, automated dilution, and any combination thereof.

16. A system comprising:

a wellbore extending into a subterranean formation;

a gas chromatograph configured to measure concentrations of one or more components of a multi-component sample gas at a calibration setting; and an information handling system communicatively coupled to the gas chromatograph, wherein the calibration setting accounts for one or more non-linearities of the measured concentrations based at least in part on calibration data, the calibration data representing one or more results of one or more linear ratio tests.

17. The system of claim 16, wherein the one or more linear ratio tests comprise:

purging a vessel with a purge gas having a known concentration of at least a chemical of interest;

connecting a pump to a gas chromatograph and the vessel;

controlling pressure and flow rate of an output of the pump;

calibrating the gas chromatograph at least at an initial concentration of the purge gas;

opening the vessel to atmosphere or a non-interfering gas through a constrained port;

activating the pump, wherein dilution occurs within at least the vessel;

capturing one or more changes to concentrations of the at least a chemical of interest as a function of time;

determining linear ratios as a function of time;

adjusting a plurality of correction factors using the linear ratios as a constraint; and fitting the adjusted correction factors with one or more functions to obtain more accurate concentrations.

18. The system of claim 16, wherein the calibration setting comprises:

a plurality of correction factors derived from the one or more linear ratio tests; and one or more predicted correction factors derived from the plurality of correction factors.

19. The system of claim 18, wherein the calibration data comprises one or more multi-linear curves associated with at least one compound selected from the group consisting of methane, ethane, propane, butane, isobutane, pentane, isopentane, and any combination thereof.

20. The system of claim 16, further comprising a gas extraction system in fluidic communication with the gas chromatograph.

* * * * *